United States Patent
Kuo et al.

(10) Patent No.: US 9,657,063 B2
(45) Date of Patent: May 23, 2017

(54) PORCINE CIRCOVIRUS TYPE-2 (PCV2) SUBUNIT VACCINE

(71) Applicant: SBC VIRBAC BIOTECH CO., LTD., Taipei (TW)

(72) Inventors: Tsun-Yung Kuo, I-Lan (TW); Hsu-Chung Gabriel Chen, Taipei (TW); Shu-Hsiang Yang, New Taipei (TW); Yu-San Chen, Taichung (TW)

(73) Assignee: SBC VIRBAC LIMITED, Causeway Bay (HK)

( * ) Notice: Subject to any disclaimer, the term of this patent is extended or adjusted under 35 U.S.C. 154(b) by 0 days.

(21) Appl. No.: 14/363,341

(22) PCT Filed: Dec. 5, 2012

(86) PCT No.: PCT/CN2012/085907
§ 371 (c)(1),
(2) Date: Jun. 6, 2014

(87) PCT Pub. No.: WO2013/083036
PCT Pub. Date: Jun. 13, 2013

(65) Prior Publication Data
US 2014/0348864 A1    Nov. 27, 2014

Related U.S. Application Data

(60) Provisional application No. 61/567,248, filed on Dec. 6, 2011.

(51) Int. Cl.
| | | |
|---|---|---|
| *C07K 14/005* | (2006.01) | |
| *A61K 39/12* | (2006.01) | |
| *C07K 14/21* | (2006.01) | |
| *C12N 7/00* | (2006.01) | |
| *C07K 5/103* | (2006.01) | |
| *A61K 39/00* | (2006.01) | |

(52) U.S. Cl.
CPC ............ *C07K 14/005* (2013.01); *A61K 39/12* (2013.01); *C07K 5/101* (2013.01); *C07K 14/21* (2013.01); *C12N 7/00* (2013.01); *A61K 2039/552* (2013.01); *A61K 2039/55544* (2013.01); *A61K 2039/55566* (2013.01); *A61K 2039/6037* (2013.01); *C07K 2319/04* (2013.01); *C07K 2319/55* (2013.01); *C12N 2750/10022* (2013.01); *C12N 2750/10034* (2013.01)

(58) Field of Classification Search
None
See application file for complete search history.

(56) References Cited

U.S. PATENT DOCUMENTS

| | | |
|---|---|---|
| 2008/0206271 A1 | 8/2008 | Liao et al. |
| 2009/0017064 A1 | 1/2009 | Wu et al. |
| 2012/0164170 A1 | 6/2012 | Kuo et al. |

FOREIGN PATENT DOCUMENTS

| | | |
|---|---|---|
| CN | 101104641 A | 1/2008 |
| CN | 101180406 A | 5/2008 |
| CN | 101884787 A | 11/2010 |
| CN | 101936993 A | 1/2011 |
| CN | 101948849 A | 1/2011 |
| CN | 102127533 A | 7/2011 |
| GB | 2467722 A | 8/2010 |
| TW | I221774 B | 10/2004 |
| TW | 200804426 A | 1/2008 |
| TW | I314559 B | 9/2009 |
| WO | 9929871 A2 | 6/1999 |

OTHER PUBLICATIONS

Gamage et al. Immunogenicity of bacteriophage lambda particles displaying porcine Circovirus 2 (PCV2) capsid protein epitopes. Vaccine. Nov. 5, 2009;27(47):6595-604. Epub Aug. 25, 2009.*
GenBank: DQ629119.1. Porcine circovirus 2 isolate iB2, complete genome. Dated Jun. 14, 2007.*
GenBank: AAF87237.1, putative capsid protein [Porcine circovirus-2]. Dated Jul. 23, 2000.*
Liu et al. The ORF3 Protein of Porcine Circovirus Type 2 is Involved in Viral Pathogenesis In Vivo. J. Virol., 2006, 80(10): 5065-5073.*
Ju et al. Immunogenicity of a recombinant pseudorabies virus expressing ORF1-ORF2 fusion protein of porcine circovirus type 2. Vet Microbiol. Aug. 30, 2005;109(3-4):179-90.*
Yin et al. An ELISA Based on a Truncated Soluble ORF2 Protein for the Detection of PCV2 Antibodies in Domestic Pigs. Virologica Sinica, Jun. 2010, 25 (3):191-198.*
GenBank: AAN62766.1. putative capsid protein [Porcine circovirus-2]. Nov. 6, 2002.*
Lou et al. Expression and antigenicity characterization for truncated capsid protein of porcine circovirus type 2. Can J Vet Res. Jan. 2011;75(1):61-4.*
Lou et al. Prokaryotic expression and potential application of the truncated PCV-2 capsid protein. Virol Sin. Apr. 2010;25(2):86-97.*
Guo, Longjun et al., "Identification of Antigen Epitope Located at the N Terminal Nuclear Localization Signal Region in Capsid Protein of Porcine Circovirus Type 2 (PCV2)", Scientia Agricura Sinica, Jul. 2010, vol. 43, No. 7, pp. 1480-1486, China.

(Continued)

*Primary Examiner* — Nick Zou

(74) *Attorney, Agent, or Firm* — Locke Lord LLP; Tim Tingkang Xia, Esq.

(57) ABSTRACT

A porcine circovirus type-2 (PCV2) immunogenic composition includes an antigenic peptide. The antigenic peptide is a non-arginine-rich peptide of a PCV2 open reading frame 2 (ORF2) and/or a recombinant fusion protein having the non-arginine-rich peptide of the PCV2 ORF2, a PE peptide, and a KDEL signal peptide. The number of arginines of the non-arginine-rich peptide of the PCV2 ORF2 is not greater than half of the number of arginines of the arginine-rich domain of the N terminal of the PCV2 ORF2.

6 Claims, 5 Drawing Sheets

(56) References Cited

OTHER PUBLICATIONS

State Intellectual Property Office of P. R. China (ISA/CN), "International Search Report", for International application No. PCT/CN2012/085907, mailing date as of Mar. 14, 2013, China.

Shao-Bin Shang et al. Fine mapping of antigenic epitopes on capsid proteins of porcine circovirus and antigenic phenotype of porcine circovirus Type 2, Molecular Immunology, 2009, 327-334, 46.

Zhong-Zi Lou et al. Prokaryotic expression and potential application of the truncated PCV-2 capsid protein, Virologica Sinica, 2010, 86-97, 25.

EBI accession No. UniProt: Q80QW2. Capsid protein [Porcine circovirus 2] Jun. 1, 2003.

K. Dupont et al. Genomic analysis of PCV2 isolates from Danish archives and a current PMWS case-control study supports a shift in genotypes with time, Veterinary Microbiology, 2008, 56-64, 128.

EBI accession No. UniProt: A9QMC6. Capsid protein [Porcine circovirus 2] Feb. 5, 2008.

Fang Wang et al. Genetic Variation Analysis of Chinese Strains of Porcine Circovirus Type 2, Virus Research, 2009, 151-156, 145.

EBI accession No. UniProt: A5A446. Capsid protein [Porcine circovirus 2] May 29, 2007.

EBI accession No. UniProt: Q5XVM5. Capsid protein [Porcine circovirus 2] Nov. 23, 2004.

EBI accession No. UniProt: Q20QW2. Polymerase acidic protein [Influenza A virus] Apr. 18, 2006.

Long-Jun Guo et al. Identification of antigen epitope Located at the N Terminal Nuclear Localization Signal Region in Capsid Protein of Porcine Circovirus Type 2 (PCV2), Scientia Agriculture Sinica, 2010,1480-1486, 43(7).

Lorenzo Fraile et al. Prevalence of Infection with Porcine Circovirus-2 (PCV-2) and porcine reproductive and respiratory syndrome virus (PRRSV) in an integrated swine production system experiencing postweaning multisystemic wasting Syndrome, The Canadian Journal of Veterinary Research, 2009, 308-312, 73.

\* cited by examiner

US 9,657,063 B2

PORCINE CIRCOVIRUS TYPE-2 (PCV2) SUBUNIT VACCINE

BACKGROUND OF THE INVENTION

1. Field of the Invention

The invention is related to a porcine circovirus type 2 (PCV2) subunit vaccine, particularly to a PCV2 subunit vaccine having a peptide of PCV2 open reading frame (ORF2) that can be abundantly expressed as an antigen and an additionally proper carrier or adjuvant.

2. Description of the Prior Art

It is known that porcine circovirus type 2 (PCV2) is related to postweaning multisystemic wasting syndrome (PMWS) and porcine dermatitis and nephropathy syndrome (PDNS). PMWS was first found in pigs in Canada in 1991 and has been reported subsequently around the world. The syndrome has caused a huge loss in swine production industry worldwide. Main symptoms of PMWS include progressive weight loss, tachypnea, dyspnea, jaundice, et cetera. Visibly pathological changes in tissue include lymphocytic and granulomatous infiltrate, lymphadenopathy, lymphocytic and granulomatous hepatitis, and nephritis.

Porcine circovirus (PCV) was first recognized in a pig kidney cell line (PK-15, ATCC CCL33) in 1982. Although the porcine circovirus can continuously contaminate PK-15 cells, the virus does not cause cytopathic effect (CPE) in the contaminated PK-15 cells. Even though the porcine circovirus can infect pigs, it does not cause lesions in the infected pigs. The virus is named porcine circovirus type 1 (PCV1). PCV1 is an icosahedron, single-stranded DNA virus with a circular genome of 1,759 bp. The PK-15-derived PCV was classified in the Circoviridae family in 1995.

The PK-15-derived PCV1 is considered apathogenic. In contrast, the virus mutation isolated from pigs with PMWS in 1997 is pathogenic and is named porcine circovirus type 2 (PCV2). Postweaning Multisystemic Wasting Syndrome (PMWS) is a highly contagious pig disease. It mainly infects pregnant sows and their piglets and seriously affects health of pigs.

PCV2 is a single-stranded, circular DNA virus with a diameter of 17 nm, and its genome size is 1.76 kb. Genomic analysis with software shows a total of 11 open reading frames (ORFs) transcribed in the clockwise and counter-clockwise directions. Among the 11 ORFs, ORF1 and ORF2 are probably the most important genes. ORF1 gene encodes Rep and Rep' proteins, which are related to virus replication. It is known that ORF2 gene encodes immunogenic structure capsid protein of PCV2, which is used to induce immune response in organisms.

Inactivated PCV2 vaccine is the most common commercially available PCV2 vaccine. However, developing inactivated vaccine requires cell lines to be free of contaminant, and the possibility of incomplete inactivation of the virus by chemicals is the most significant disadvantage of inactivated vaccine. Another disadvantage is that the antigenic structures of the virus may be altered by chemical treatment, leading to failure to induce sufficient immune response to eliminate the virus and failure to protect pigs from infection of the disease. Therefore, developing inactivated vaccine can be difficult and costly, and vaccine safety may be a concern.

Unlike inactivated vaccine, in which the whole virus is the vaccine antigen, subunit vaccine uses a part of proteins from the pathogen as antigen protein, and the antigen protein is inoculated into animals or humans to induce immunity. Subunit vaccine can be prepared by cloning genes encoding antigen proteins from pathogens and then producing large amounts of the antigen proteins by genetic engineering. Safety is the most significant advantage of subunit vaccine because it uses parts of a pathogen, instead of a whole pathogen, to inoculate pigs without the issue of incomplete inactivation. Conventional PCV2 subunit vaccine uses PCV2 ORF2 protein as the antigen protein; however, the protein expression level of full-length PCV2 ORF2 protein in prokaryotic expression systems is quite low and does not meet the requirements of vaccine production. Therefore, developing antigen fragments of PCV2 ORF2 that can be highly expressed in biological expression systems is helpful to commercial application of PCV2 subunit vaccine.

SUMMARY OF THE INVENTION

The disclosure provides DNA sequences encoding protein fragments of PCV2 ORF2, and the protein fragments of PCV2 ORF2 can be highly expressed in biological expression systems.

The disclosure also provides PCV2 subunit vaccine in which protein fragments of PCV2 ORF2 that can be highly expressed in biological expression systems are used as antigen proteins to be inoculated into animals to induce sufficient immunity against PCV2 infection in the animals.

The disclosure further provides subunit vaccine developed by genetic engineering to produce low-cost, high-purity, and good safety PCV2 subunit vaccine with simple production process.

Due to the fact that protein expression level of full-length PCV2 ORF2 protein in biological expression systems is quite low, genetic engineering was used to achieve the objects above. DNA sequences (such as SEQ ID NO: 1) that encode full-length PCV2 ORF2 proteins were cut into fragments of different sizes, and the DNA fragments were inserted into expression vectors and then expressed in hosts. The levels of the expressed proteins were evaluated to determine which DNA fragments can produce high levels of proteins in protein expression systems.

Results of protein sequence analysis and protein expression tests show that there are about 30 arginines in a full-length PCV2 ORF2 protein, in which at least two thirds of the arginines locate at the N terminus of the PCV2 ORF2 protein. The more arginines at the N terminus being deleted, the higher level the ORF2 protein fragment being expressed. Further, after the first 234 nucleotides at the 5' end of a full-length DNA sequence of PCV2 ORF2 is deleted, the protein fragment encoded by the remaining DNA fragment (i.e. from nucleotide 235 at the 5' end to a stop codon) can be highly expressed.

Therefore, the PCV2 subunit vaccine provided in the disclosure comprises an antigenic peptide of PCV2 with proper carrier or adjuvant. The antigenic peptide can be highly expressed in expression systems and is a non-arginine-rich peptide of the PCV2 ORF2. The number of arginines of the non-arginine-rich peptide of the PCV2 ORF2 are not more than half (½) of the number of arginines of an arginine-rich domain at the N terminus of the full-length PCV2 ORF2. In an embodiment, when the number of arginines of the arginine-rich domain at the N terminus of a full-length PCV2 ORF2 is 20, the number of arginines of the non-arginine-rich peptide of the PCV2 ORF2 is one of the integers between 0 and 10. In another embodiment, when the number of arginines of the arginine-rich domain at the N terminus of a full-length PCV2 ORF2 is 21, the number of arginines of the non-arginine-rich peptide of the PCV2 ORF2 is one of the integers between 0 and 10. In yet another embodiment, when the number of arginines of the arginine-rich domain at the N terminus of a full-length PCV2 ORF2 is 22, the number of arginines of the non-arginine-rich peptide of the PCV2 ORF2 is one of the integers between 0 and 11.

In an embodiment, the arginine-rich domain has residues 1-78 at the N terminus of a full-length PCV2 ORF2 (which are encoded by nucleotides 1-234 at the 5' end of a full-length DNA sequence of the PCV2 ORF2). In an embodiment, the non-arginine-rich peptide has the peptide sequence from residue 79 to the last amino acid residue at the C terminus of a full-length PCV2 ORF2 (which is encoded by the DNA sequence from nucleotide 235 at the 5' end to a stop codon at the 3' end of a full-length DNA sequence of the PCV2 ORF2).

The PCV2 ORF2 disclosed herein has a full-length peptide sequence having at least 80%, preferably 85%, more preferably 90%, even more preferably 91%, 92%, 93%, 94%, 95%, 96%, 97%, 98%, or 99% homology to one of SEQ ID NO: 2, SEQ ID NO: 16, SEQ ID NO: 20, SEQ ID NO: 51, and SEQ ID NO: 53. In a preferable embodiment, the PCV2 ORF2 disclosed herein has a full-length peptide sequence of one of SEQ ID NO: 2, SEQ ID NO: 16, SEQ ID NO: 20, SEQ ID NO: 51, and SEQ ID NO: 53.

In addition, the disclosure provides a PCV2 ORF2 fusion protein as an antigenic peptide by using the functions of the receptor binding domain I and the transmembrane targeting domain II of *Pseudomonas aeruginosa* exotoxin A (i.e. the "PE protein") and an endoplasmic reticulum (ER) retention signal (i.e. the "KDEL signal peptide").

The PE protein of *Pseudomonas aeruginosa* can be used as a guide of a target protein to its target location by the following procedure. First, the receptor binding domain of *Pseudomonas aeruginosa* exotoxin A is responsible for binding to receptors on the membrane of the target cells (CD8+ T cells), and then the ligand-receptor complexes enter the endosomes of the target cells through endocytosis. After enzymatic cleavage by a protease in the endosomes, truncated protein fragments (containing the transmembrane targeting domain and the linked target protein) are delivered into the Golgi bodies and the endoplasmic reticulum (ER) and further translocated into the cytoplasm of the target cells by the transmembrane targeting domain.

Furthermore, when a KDEL signal peptide is linked at the C terminus of a target protein, the target protein will be transported to the ER by the KDEL signal peptide and then interact in the ER.

Therefore, the disclosure provides a PCV2 ORF2 fusion protein as an antigenic peptide by using the functions of the PE protein and the KDEL signal peptide. PE protein and KDEL signal peptide were fused with a PCV2 ORF2 protein fragment at the N and C terminuses, respectively, to produce the fusion protein (PE-ORF2 fragment-KDEL) to be inoculated into animals to induce sufficient immunity against PCV2 infection in the animals.

In some embodiments, the antigenic peptides used herein include, but not limited to, PCV2 ORF2 fragments. The ORF2 fragments have a peptide sequence having at least 80%, preferably 85%, more preferably 90%, even more preferably 91%, 92%, 93%, 94%, 95%, 96%, 97%, 98%, or 99% homology to one of SEQ ID NO: 6, SEQ ID NO: 8, SEQ ID NO: 10, SEQ ID NO: 12, SEQ ID NO: 18, SEQ ID NO: 22, SEQ ID NO: 55, and SEQ ID NO: 57. In a preferable embodiment, the PCV2 ORF2 fragments has a peptide sequence of one of SEQ ID NO: 6, SEQ ID NO: 8, SEQ ID NO: 10, SEQ ID NO: 12, SEQ ID NO: 18, SEQ ID NO: 22, SEQ ID NO: 55, and SEQ ID NO: 57, and were obtained by genetic engineering. DNA sequences (SEQ ID NOs: 5, 7, 9, 11, 17, 21, 54, 56) encoding the PCV2 ORF2 fragments were cloned into expression vectors to form plasmids containing a DNA fragment encoding an antigenic peptide. The plasmids were then transformed into host cells to express the antigenic peptides.

The fusion proteins (PE-ORF2 fragment-KDEL) disclosed herein were obtained by genetic engineering. DNA sequences (SEQ ID NOs: 5, 7, 9, 11, 17, 21, 54, 56) encoding the PCV2 ORF2 fragments, DNA sequence (SEQ ID NO: 34) encoding the PE protein, and the DNA sequence (SEQ ID NO: 30) encoding the KDEL signal peptide were cloned into expression vectors to form plasmids containing a DNA fragment encoding a fusion protein. The plasmids were then transformed into host cells to express the fusion protein.

The expression vectors include but not limited to pET vectors and pGEX vectors. In an embodiment, the expression vector is pET24a. The expression systems (host cells) include but not limited to prokaryotic expression systems (such as *Escherichia coli* (*E. coli.*)), eukaryotic expression systems (such as animal cells (for example, CHO cell) and plant cells). In an embodiment, the expression system is *E. coli*.

The adjuvant includes, but not limited to, aqueous adjuvant (such as aluminum hydroxide), potassium alum, Freund's Incomplete Adjuvant, oil adjuvant, water-soluble adjuvant, or water-in-oil-in-water (W/O/W) emulsion adjuvant. In an embodiment, the adjuvant is oil adjuvant.

The immunogenic composition disclosed herein further comprises antigenic peptides of other PCV2 ORFs. The other PCV2 ORFs include, but not limited to, ORF1 and ORF3. In addition, the immunogenic composition disclosed herein further comprises a pathogen antigen. The pathogen antigen is selected from the group consisting of antigen of Swine influenza virus (SIV), antigen of porcine reproductive and respiratory syndrome virus (PRRSV), antigen of mycoplasma, antigen of porcine parvovirus (PPV), antigen of erysipelas, and antigen of pseudorabies (Aujeszky's disease) virus.

In addition, the immunogenic composition disclosed herein further comprises one or more than one of the followings: vehicles, solvent, emulsifier, suspending agent, decomposer, binding agent, excipient, stabilizing agent, chelating agent, diluent, gelling agent, preservative, lubricant, surfactant, adjuvant, and biological carriers.

The meaning of the technical and scientific terms as described herein can be clearly understood by a person of ordinary skill in the art.

The present invention is described in more detail in the following illustrative examples. Although the examples may represent only selected embodiments of the invention, it should be understood that the following examples are illustrative and not limiting.

DETAILED DESCRIPTION OF THE PREFERRED EMBODIMENT

Example 1

Figure 1:
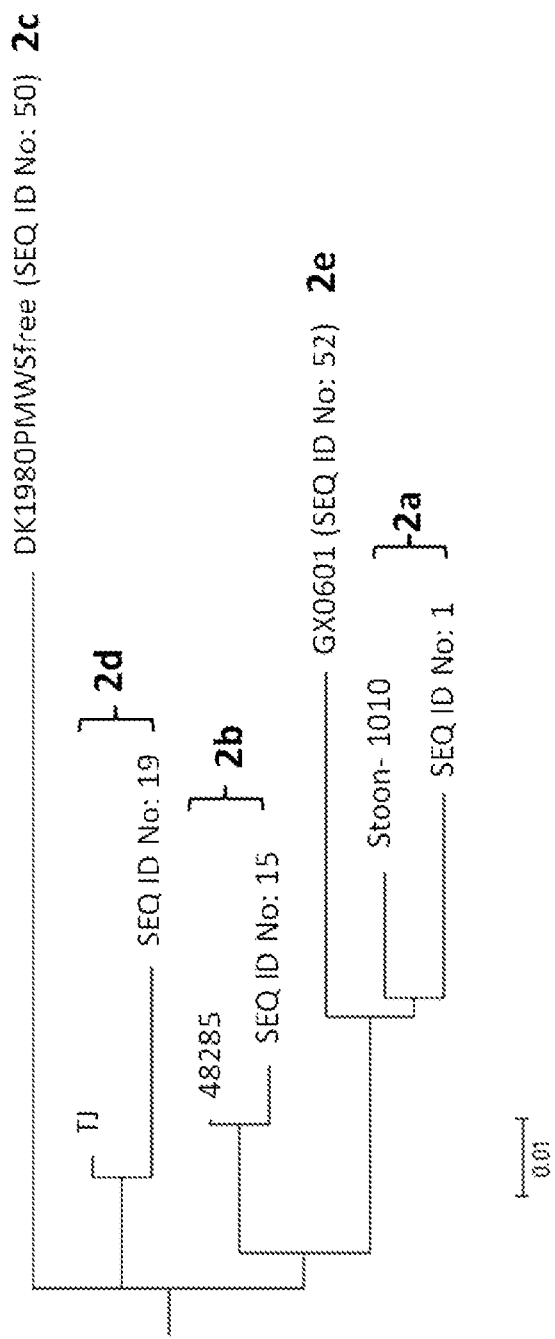
FIG. 1 provides phylogenetic analysis of PCV2 genome sequences.
Figure 2:
FIG. 2 illustrates a schematic diagram of the PCV2 ORF2 fragments, in which pF1, pF2, pF3, pF4, pR1, pR2, and pR3 are PCR primers.
Figure 3:
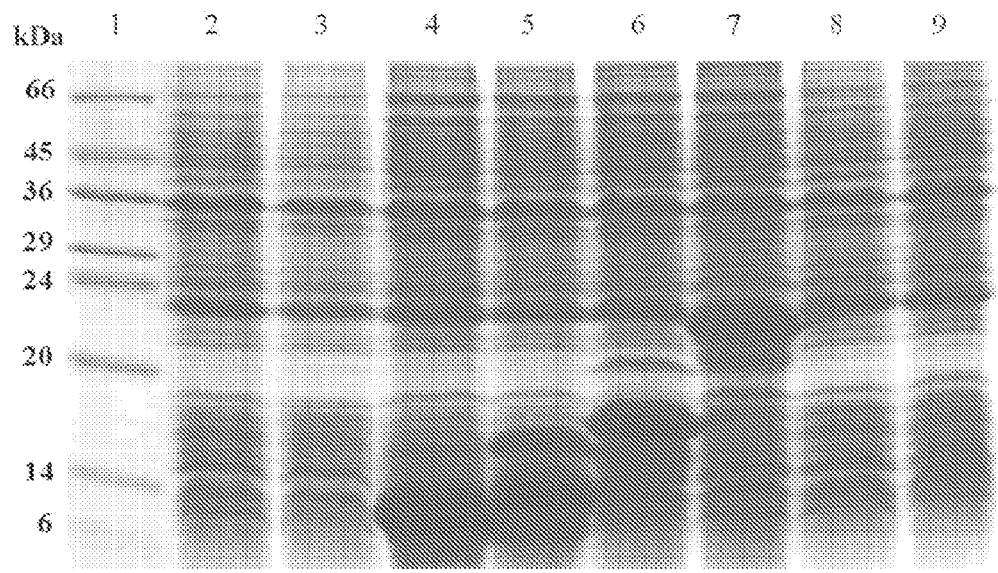
FIG. 3 shows the results of SDS-PAGE analysis of recombinant proteins of different PCV2 2a-ORF2 fragments expressed in *E. coli*. Total proteins of *E. coli* were collected at 6 hours after IPTG induction and then resolved by a 15% SDS-PAGE, in which lanes 1-9 show molecular weight ladders, empty pET24a vector (as negative control), PCV2 ORF2 2a-F1 fragment (12.7 KDa), PCV2 ORF2 2a-F2 fragment (11.6 KDa), PCV2 ORF2 2a-F3 fragment (12.1 KDa), PCV2 ORF2 2a-F4 fragment (16.5 KDa), PCV2 ORF2 2a-F5 fragment (21.4 KDa), PCV2 ORF2 2a-F6 fragment (20.8 KDa), and full-length PCV2 2a-ORF2 (27.5 KDa), respectively.
Figure 4:
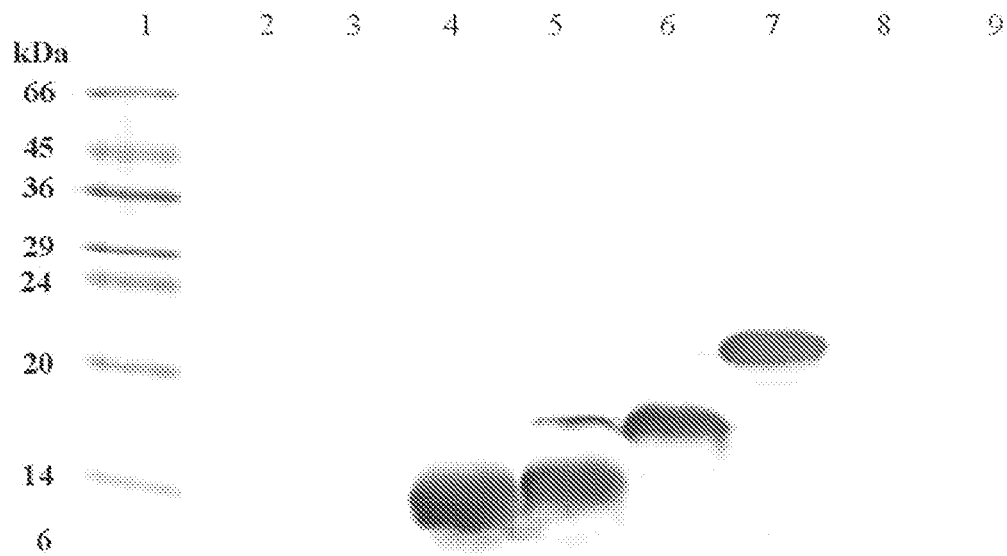
FIG. 4 provides the results of western bolt of recombinant proteins of different PCV2 2a-ORF2 fragments. Lanes 1-9 show molecular weight ladders, empty pET24a vector (as negative control), PCV2 ORF2 2a-F1 fragment (12.7 KDa), PCV2 ORF2 2a-F2 fragment (11.6 KDa), PCV2 ORF2 2a-F3 fragment (12.1 KDa), PCV2 ORF2 2a-F4 fragment (16.5 KDa), PCV2 ORF2 2a-F5 fragment (21.4 KDa), PCV2 ORF2 2a-F6 fragment (20.8 KDa), and full-length PCV2 2a-ORF2 (27.5 KDa), respectively.

Construction and Determination of Antigenic Peptides of PCV2 Subunit Vaccine

Due to the fact that protein expression level of full-length PCV2 ORF2 protein in biological expression systems is quite low, DNA sequences that encode full-length PCV2 ORF2 proteins are cut into fragments of different sizes, and the DNA fragments are inserted into expression vectors and then expressed in hosts. The levels of the expressed proteins are evaluated to determine which DNA fragments can produce high levels of proteins in protein expression systems.

A commonly used prokaryotic expression system (*Escherichia coli*) is used in the following examples for analysis and illustration.

1. Amplification of PCV2 ORF2 Gene Fragments of Different Sizes

The full-length PCV2 ORF2 gene used in this example has a sequence of SEQ ID NO: 1. PCV2 ORF2 gene sequences provided by Wang et al. (Wang et al., Virus Research 2009, Genetic variation analysis of Chinese strains of porcine circovirus type 2.) are used as standard sequences for phylogenetic analysis of SEQ ID NO: 1. The result shows that the PCV2 ORF2 sequence (SEQ ID NO: 1) belongs to PCV2 2a subgroup (as shown in FIG. 1). Primers (as shown in Table 1) were designed to amplify different sizes of fragments of the PCV2 2a ORF2 gene (2a-ORF2) by polymerase chain reaction (PCR).

As shown in FIG. 2, the full-length 2a-ORF2 gene was amplified with specific primers pF1 (forward primer) and pR1 (reverse primer) by PCR. The full-length 2a-ORF2 gene (2a-ORF2) has the DNA sequence of SEQ ID NO: 1, and the different sizes of fragments of the PCV2 2a-ORF2 are named 2a-F1, 2a-F2, 2a-F3, 2a-F4, 2a-F5, and 2a-F6, respectively. The 2a-F1 fragment has the DNA sequence of SEQ ID NO: 3, which is nucleotides 1-234 at the 5' end of 2a-ORF2. The 2a-F2 fragment has the DNA sequence of SEQ ID NO: 5, which is nucleotides 235-468 at the 5' end of 2a-ORF2. The 2a-F3 fragment has the DNA sequence of SEQ ID NO: 7, which is nucleotides 469-699 at the 5' end of 2a-ORF2. The 2a-F4 fragment has the DNA sequence of SEQ ID NO: 9, which is nucleotides 349-699 at the 5' end of 2a-ORF2. The 2a-F5 fragment has the DNA sequence of SEQ ID NO: 11, which is nucleotides 235-699 at the 5' end of 2a-ORF2. The 2a-F6 fragment has the DNA sequence of SEQ ID NO: 13, which is nucleotides 1-468 at the 5' end of 2a-ORF2. All forward primers contain a Hind III restriction site, and all reverse primers contain an Xho I restriction site.

TABLE 1

Sequence listing of primers for amplication of different sizes of fragments of PCV2 ORF2 gene

| Fragment | Primer | | Sequence[Note] | |
|---|---|---|---|---|
| ORF2 | pF1 | Forward primer | CCCAAGCTTGCATGACGT ATCCAAGGAGGCG | SEQ ID NO: 23 |
| | pR1 | Reverse primer | CCG CTCGAG GGGTTT AAGTGGGGGGTCTTTA | SEQ ID NO: 24 |
| F1 | pF1 | Forward primer | CCCAAGCTTGCATGACGT ATCCAAGGAGGCG | SEQ ID NO: 23 |
| | pR3 | Reverse primer | CCG CTCGAG GTCGTT AATATTAAATCTCATC | SEQ ID NO: 28 |
| F2 | pF2 | Forward primer | CCCAAGCTTGCTTTGTTC CCCCGGGAGGGGG | SEQ ID NO: 25 |
| | pR2 | Reverse primer | CCG CTCGAG GTAGGA GAAGGGTTGGGGGATT | SEQ ID NO: 26 |
| F3 | pF3 | Forward primer | CCCAAGCTTGCCACTCCC GGTACTTTACCCC | SEQ ID NO: 27 |
| | pR1 | Reverse primer | CCG CTCGAG GGGTTT AAGTGGGGGGTCTTTA | SEQ ID NO: 24 |
| F4 | pF4 | Forward primer | CCCAAGCTTGCGGAGTGG GCTCCACTGCTGT | SEQ ID NO: 29 |
| | pR1 | Reverse primer | CCG CTCGAG GGGTTT AAGTGGGGGGTCTTTA | SEQ ID NO: 24 |
| F5 | pF2 | Forward primer | CCCAAGCTTGCTTTGTTC CCCCGGGAGGGGG | SEQ ID NO: 25 |
| | pR1 | Reverse primer | CCG CTCGAG GGGTTT AAGTGGGGGGTCTTTA | SEQ ID NO: 24 |
| F6 | pF1 | Forward primer | CCCAAGCTTGCATGACGT ATCCAAGGAGGCG | SEQ ID NO: 23 |
| | pR2 | Reverse primer | CCG CTCGAG GTAGGA GAAGGGTTGGGGGATT | SEQ ID NO: 26 |

Note:
Sequences marked with "____" underneath are the sequences of Hind III restriction site (AAGCTT), and sequences marked with "~~~~" underneath are the sequences of Xho I restriction site (CTCGAG).

Conditions for PCR reaction comprises: 95° C. for 5 minutes, 25 cycles of 95° C. for 30 seconds, 55° C. for 30 seconds, and 72° C. for 30 seconds, and 72° C. for 5 minutes for elongation. Sizes of the PCR products 2a-ORF2, 2a-F1, 2a-F2, 2a-F3, 2a-F4, 2a-F5, and 2a-F6 are 699 bp, 234 bp, 234 bp, 231 bp, 351 bp, 465 bp, and 468 bp, respectively, and confirmed by 2% agarose electrophoresis. After confirmation, the PCR products were purified with PCR-M purification kit (Viogene).

2. Construction of pET24a Plasmids Containing Different Sizes of Fragments of PCV2 ORF2

One (1) μg of the purified PCR products and 1 μg of pET24a expression vector (Novagen) were digested with two restriction enzymes (New England Biolabs), 1 μl of Hind III and 1 μl of Xho I, respectively, for 8 hours at 37° C. After restriction enzyme cleavage reaction, the digested PCR products and pET24a expression vector were purified with PCR-M Clean up System (Viogene) respectively. The purified PCR products were ligated with the purified pET24a expression vector to form plasmids pET24a-2a-F1, pET24a-2a-F2, pET24a-2a-F3, pET24a-2a-F4, pET24a-2a-F5, pET24a-2a-F6, and pET24a-2a-ORF2, and then the plasmids were transformed into host cells (*E. coli*). Transformants containing the PCR products were selected, and DNA sequences were confirmed by DNA sequencing. Bacteria containing the plasmids above were then obtained.

3. Protein Expression and Confirmation of Different Sizes of Fragments of PCV2 ORF2

Bacteria containing the plasmids above were incubated in 2 ml of LB medium at 37° C. for 16-18 hours and then inoculated at a ratio of 1:50 in LB medium containing 25 μg/ml kanamycin to be further incubated in a 37° C., 200 rpm incubator until the O.D. 600 nm is 0.6. After that, β-D-thiogalactoside (IPTG) was added to a final concentration of 1 mM, and the *E. coli* host cells were incubated in a 37° C., 200 rpm incubator for 6 more hours. Then, 1 ml of the *E. coli* host cells was centrifuged at 10,000×g, and the pellet was treated with B-PE® Bacterial Protein Extraction (purchased from PIERCE) to check whether the recombinant proteins are soluble proteins or in inclusion bodies by the following steps. The pellet was added in 40 μl of reagent, mixed with a vortex shaker for 1 minute, and centrifuged at 10,000×g to separate soluble proteins (upper part) from insoluble inclusion bodies (lower part). The soluble proteins were dissolved in 1×SDS-PAGE sample buffer, and the pellet was added in 2×SDS-PAGE sample buffer. The samples were placed in a heat block at 100° C. for 20 minutes and then centrifuged. The supernatant was analyzed by 15% SDS-PAGE to measure the expression of the recombinant proteins.

The recombinant proteins were produced by inducing bacterial culture with IPTG. The 2a-ORF2 recombinant protein has the amino acid sequence of SEQ ID NO: 2. The 2a-F1 recombinant protein has the amino acid sequence of SEQ ID NO: 4. The 2a-F2 recombinant protein has the amino acid sequence of SEQ ID NO: 6. The 2a-F3 recombinant protein has the amino acid sequence of SEQ ID NO: 8. The 2a-F4 recombinant protein has the amino acid sequence of SEQ ID NO: 10. The 2a-F5 recombinant protein has the amino acid sequence of SEQ ID NO: 12. The 2a-F6 recombinant protein has the amino acid sequence of SEQ ID NO: 14.

Expression of the recombinant proteins was analyzed by SDS-PAGE, and the results are shown in FIG. 3, where lane 1 shows molecular weight ladders, lane 2 shows the negative control (empty pET24a vector), lane 3 shows the 2a-F1 recombinant protein (12.7 KDa), lane 4 shows the 2a-F2 recombinant protein (11.6 KDa), lane 5 shows the 2a-F3 recombinant protein (12.1 KDa), lane 6 shows the 2a-F4 recombinant protein (16.5 KDa), lane 7 shows the 2a-F5 recombinant protein (21.4 KDa), lane 8 shows the 2a-F6 recombinant protein (20.8 KDa), and lane 9 shows full-length 2a-ORF2 recombinant protein (27.5 KDa). Among the 6 fragments of 2a-ORF2, fragments 2a-F2, 2a-F3, 2a-F4, and 2a-F5 were expressed in large quantities (FIG. 3, lanes 4-7). The estimated sizes of fragments 2a-F2, 2a-F3, 2a-F4, and 2a-F5 proteins match their actual sizes of 11.6 kDa, 12.1 kDa, 16.5 kDa, and 21.4 kDa, respectively.

Next, western blotting was deployed to check whether the expressed recombinant proteins are PCV2 2a-ORF2 fragments. Following electrophoresis, the SDS-PAGE was transferred onto a PVDF Nylon membrane. The resulting membrane was blocked with blocking buffer, which is TBST (10 mM Tris-HCl, pH 8.0, 150 mM NaCl, 0.1% Tween 20) containing 5% skim milk, for 1 h at room temperature to prevent non-specific binding of proteins. After that, the proteins were identified using alkaline phosphatase (AP)-conjugated mouse anti-6×his monoclonal antibodies against the 6×his-tag fusion proteins for 1 hour at room temperature, followed by 6 times of wash with TBST, 5 minutes for each. After wash, NBT/BCIP substrate (Bio-Rad) was added. After 10 minutes, the reaction was stopped by adding water.

The results of western blot are shown in FIG. 4, where lane 1 shows molecular weight ladders, lane 2 shows the negative control (empty pET24a vector), lane 3 shows the 2a-F1 recombinant protein (12.7 KDa), lane 4 shows the 2a-F2 recombinant protein (11.6 KDa), lane 5 shows the 2a-F3 recombinant protein (12.1 KDa), lane 6 shows the 2a-F4 recombinant protein (16.5 KDa), lane 7 shows the 2a-F5 recombinant protein (21.4 KDa), lane 8 shows the 2a-F6 recombinant protein (20.8 KDa), and lane 9 shows full-length 2a-ORF2 recombinant protein (27.5 KDa). The results of western blot match the results of SDS-PAGE analysis (as shown in FIG. 3). The full-length 2a-ORF2 recombinant protein cannot be expressed (FIG. 4, lane 9). Among the 6 fragments of 2a-ORF2, fragments 2a-F2, 2a-F3, 2a-F4, and 2a-F5 are expressed in large quantities (FIG. 4, lanes 4-7). The estimated sizes of fragments 2a-F2, 2a-F3, 2a-F4, and 2a-F5 proteins match their actual sizes of 11.6 kDa, 12.1 kDa, 16.5 kDa, and 21.4 kDa, respectively. However, there is no expression of the 2a-F1 recombinant protein or the 2a-F6 recombinant protein (FIG. 4, lanes 3 and 8). Since both of the 2a-F1 recombinant protein and the 2a-F6 recombinant protein contain nucleotides 1-234 at the 5' end of the full-length DNA sequence of the PCV2 2a-ORF2 (see FIG. 2), some sequences in the nucleotides 1-234 may affect expression of PCV2 ORF2 protein. Analysis of amino acid sequences of the 2a-F1 fragment (nucleotides 1-234 at the 5' end of PCV2 2a-ORF2, SEQ ID NO: 3) and the 2a-F2+2a-F3 fragment (nucleotides 235-699 (without the stop codon) at the 5' end of PCV2 2a-ORF2, SEQ ID NO: 11) shows that the arginine numbers of the amino acid sequence (SEQ ID NO: 4) of the 2a-F1 fragment are two times or more than the arginine numbers of the amino acid sequence (SEQ ID NO: 12) of the 2a-F2+2a-F3 fragment (as shown in Table 2). Analysis of addition or deletion of the arginine shows that deletion of the excessive arginine can increase protein expression of PCV2 ORF2.

TABLE 2

Analysis of Arginine Numbers of the PCV2 2a-ORF2 Amino Acid Sequence

| 2a-F1 | | | 2a-F2 + 2a-F3 | | |
|---|---|---|---|---|---|
| Codon | Amino Acid | Amount | Codon | Amino Acid | Amount |
| AGA | Arginine | 5 | AGA | Arginine | 3 |
| AGG | Arginine | 3 | AGG | Arginine | 3 |
| CGA | Arginine | 1 | CGC | Arginine | 1 |
| CGC | Arginine | 10 | CGG | Arginine | 1 |
| CGT | Arginine | 2 | CGT | Arginine | 1 |
| Total | | 21 | Total | | 9 |

Example 2

Immunogenicity Analysis of Antigenic Peptides of PCV2 Subunit Vaccine

1. Immunization of Rats

PCV2 subunit vaccine was made with the 2a-F2, 2a-F3, 2a-F4, and 2a-F5 recombinant proteins prepared in Example 1, respectively, and Freund's complete adjuvant. Rats were vaccinated with the PCV2 subunit vaccine to analyze immunogenicity of the antigenic peptides of the PCV2 subunit vaccine.

Five- to six-week-old healthy specific-pathogen-free (SPF) rats were randomly divided into 5 groups of 3 rats each. Enzyme-linked immunosorbent assay (ELISA) showed that all the 15 rats were negative for anti-PCV2 antibodies. Each rat in the 4 vaccine groups (Groups 1 to 4) was injected subcutaneously with 200 μg of recombinant protein, and the total volume of each injection was 300 μL with 1:1 (v/v) ratio of protein to adjuvant formulation. Rats in Group 5 were injected with 300 μL PBS and served as negative control. Two weeks after primary immunization (p.i.), the rats in the 4 vaccine groups were boosted with the same dose of the 4 different recombinant proteins, respectively. Serum samples were collected at weeks 0, 2, 4, and 8 post-primary immunization. All the serum samples were tested by ELISA to measure the titer of anti-PCV2 antibodies.

2. Detection of Anti-PCV2 Antibodies by ELISA

Ninety-six well plates containing PCV2 pathogen antigen (300 ng/well) were used as the ELISA plates in this example. The ELISA plates were washed 3 times with 50 mmol/L PBS (pH 7.2) containing 500 μl/L Tween-20 (i.e. PBST) for 3 to 5 minutes each time. To block the ELISA plates, 2004 of 0.15% BSA blocking solution was added to each well of the ELISA plates, and then the ELISA plates were incubated for 2 hours at 37° C. After that, the ELISA plates were washed with PBS. Rat serum samples were diluted fifty-fold (1:50) with PBS and then diluted two-fold serially. Each sample had 8 repeats. Diluted serum samples were added to the wells of the ELISA plates (100 μl/well), and the plates were incubated for 1 hour at 37° C. After incubation, the plates were washed with PBS. Anti-rat IgG antibody conjugated with alkaline phosphatase (AP) was then added to the wells. After incubating for 1 hour at 37° C., the plates were washed with PBS. For visualization of results, para-Nitrophenylphosphate (pNPP) was added to the wells. Following incubation, the reaction was stopped by adding 1M NaOH. The optical density of each well was read using optical density at 405 nm. Each sample was analyzed in duplicate, and the O.D. values of duplicates were averaged.

Figure 5:
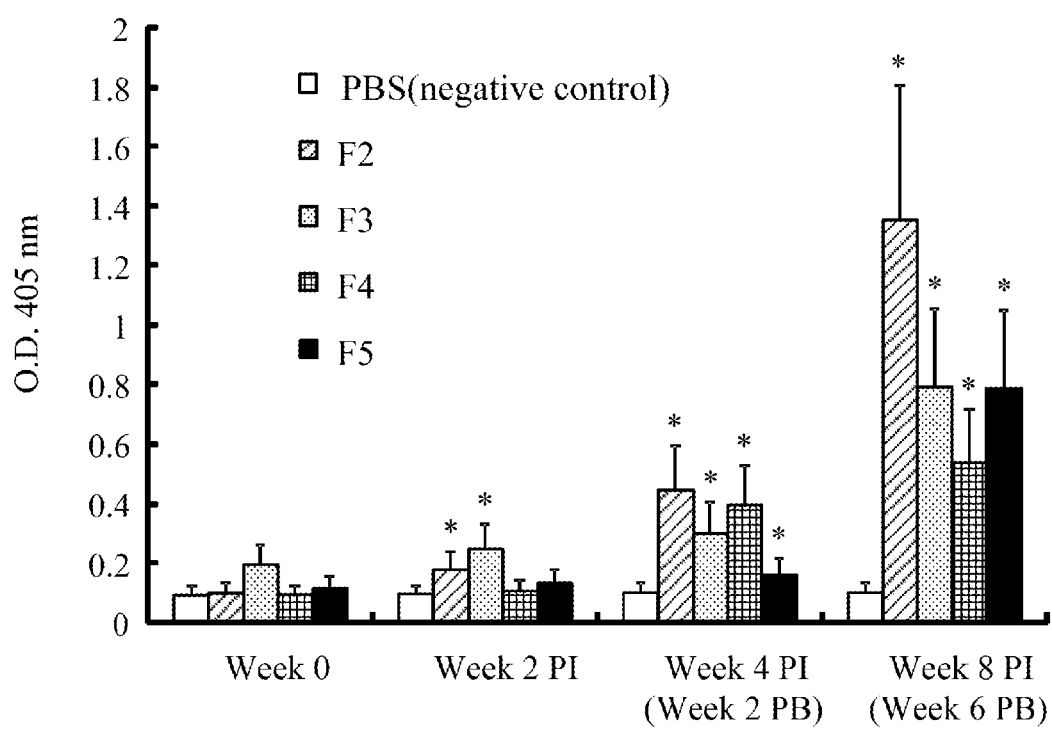
FIG. 5 provides the results of PCV2 ELISA of serum samples collected at different time points from rats vaccinated with recombinant proteins of different PCV2 2a-ORF2 fragments, respectively. *, $p<0.05$. (PI: post-immunization; PB: post-booster)

ELISA results are shown in FIG. 5. All the 2a-F2, 2a-F3, 2a-F4, and 2a-F5 recombinant proteins prepared in Example 1 are able to induce serum antibodies against PCV2 in the tested animals. Among the recombinant proteins, 2a-F2 recombinant protein (SEQ ID NO: 6) induced the highest level of serum antibody against PCV2. For statistical analysis, all groups were compared with the PBS negative control at different sampling points, and there are significant differences between the negative control and each vaccination group (p<0.05).

Furthermore, pigs were vaccinated with the 2a-F2, 2a-F3, 2a-F4, and 2a-F5 recombinant proteins, respectively, and all the recombinant proteins were able to induce serum antibodies against PCV2 in pigs. In addition, the vaccinated pigs were challenged with PCV2 virus to evaluate the efficacy of the recombinant proteins. First, the recombinant proteins were formulated as subunit vaccine and injected into pigs. Then, the pigs were challenged with PCV2 virus. The results show that the protection rates of immunization groups are higher then that of the negative control (no vaccination). The protection rates used herein include a decrease in viremia and alleviation of PCV2 symptoms. Therefore, the results show that the PCV2 subunit vaccine prepared with the recombinant proteins can effectively induce immunity in animals and increase survival rate of the animals.

Example 3

Construction and Expression of Antigenic Peptides of PCV2 2a Subunit Vaccine The results in Example 2 show that among the recombinant proteins, the F2 peptide of PCV2 ORF2 induces the highest level of serum antibody against PCV2. In order to enhance the immunogenicity of PCV2 subunit vaccine, receptor binding domain I and transmembrane targeting domain II of *Pseudomonas aeruginosa* exotoxin A (i.e. PE protein) and ER retention signal—KDEL signal peptide were fused with the 2a-F2 peptide prepared in Example 1 at the N and C terminuses, respectively, to produce a fusion protein (PE-2a-F2-KDEL) to induce sufficient immunity against PCV2 infection in animals.

The recombinant protein (PE-2a-F2-KDEL) was prepared by genetic engineering in this Example. DNA sequences encoding the proteins of interest were cloned into an expression vector to construct pET24a-PE-2a-F2-KDEL plasmid. The plasmid was induced to express PE-2a-F2-KDEL recombinant protein. First, DNA sequence (SEQ ID NO: 30) encoding KDEL signal peptide was cloned into pET24a vector to form pET24a-KDEL plasmid. After that, DNA sequence (SEQ ID NO: 5) of the 2a-F2 fragment obtained in Example 1 was cloned into pET24a-KDEL plasmid to form pET24a-2a-F2-KDEL plasmid. Finally, DNA sequence (SEQ ID NO: 34) encoding PE protein was cloned into pET24a-2a-F2-KDEL plasmid to form pET24a-PE-2a-F2-KDEL plasmid.

1. Construction of pET24a-KEDL

The DNA sequence encoding KDEL signal peptide (SEQ ID NO: 31) is shown as SEQ ID NO: 30. The DNA sequence was amplified by PCR. The sequences of KEDL specificity primers are shown as follows.

```
Forward primer (with a Hind III restriction site):
                                        (SEQ ID NO: 32)
5'-CCC AAGCTT CTCAAAAAAGACGAACTGAGAGATG
AACTGAAAGA-3'
Hind III Reverse primer (with a Xho I restriction site)
                                        (SEQ ID NO: 33)
5'-GTG CTCGAG CAGTTCGTCTTTCAGTTCATCT-3'
Xho I
```

Conditions for PCR reaction comprises: 94° C. for 3 minutes, 5 cycles of 95° C. for 1 minute, 55° C. for 1 minute, and 72° C. for 20 seconds, and 72° C. for 1 minutes for elongation. PCR product and pET24a vector were subjected to double restriction enzymes digestion with Hind III and Xho I. Thereafter, the digested PCR products and pET24a vector were purified, respectively, followed by ligation to clone the PCR product into pET24a to form pET24a-KDEL. Then, the construct pET24a-KEDL was transformed into host cells (*E. coli*) to carry out mass replication. The replicate PCR products were further confirmed by sequencing.

2. Construction of pET24a-2a-F2-KDEL

The 2a-F2 DNA sequence (SEQ ID NO: 5) obtained in Example 1 was amplified by PCR. The PCR primers are shown as follows.

```
Forward primer pF2-1
(with a Sac I restriction site):
                                    (SEQ ID NO: 38)
5'-C GAGCTC TTTGTTCCCCCGGGAGGGGGG-3'
Sac I Reverse primer pR2-1
(with a Hind III restriction site):
                                    (SEQ ID NO: 39)
5'-CCC AAGCTT GTAGGAGAAGGGTTGGGGGATT-3'
Hind III
```

Conditions for PCR reaction comprises: 95° C. for 5 minutes, 25 cycles of 95° C. for 30 seconds, 55° C. for 30 seconds, and 72° C. for 30 seconds, and 72° C. for 5 minutes for elongation. PCR product and pET24a-KDEL plasmid were subjected to double restriction enzymes digestion with Sac I and Hind III. Thereafter, the digested PCR products and pET24a-KDEL plasmid were purified, respectively, followed by ligation to clone the PCR product into pET24a-KDEL to form pET24a-2a-F2-KDEL. Then, the construct was transformed into host cells (*E. coli*) to carry out mass replication. The replicate PCR products were further confirmed by sequencing.

3. Construction of pET24a-PE-2a-F2-KDEL

The DNA sequence encoding PE protein (SEQ ID NO: 35) is shown as SEQ ID NO: 34. The DNA sequence was amplified by PCR. The sequences of PE specificity primers are shown as follows.

```
Forward primer (with a BamH I restriction site):
                                    (SEQ ID NO: 36)
5'-CG GGATCC GAAGAAGCGTTCGAC-3'
BamH I Reverse primer
(with a EcoRI and a Sac I restriction sites)
                                    (SEQ ID NO: 37)
5'-CGGAATTC GAGCTC GCAGGTCAGGCTCACCAC-3'
EcoR I Sac I
```

Conditions for PCR reaction comprises: 94° C. for 5 minutes, 30 cycles of 95° C. for 1 minute, 55° C. for 1 minute, and 72° C. for 1.5 minutes, and 72° C. for 7 minutes for elongation. PCR product and pET24a-2a-F2-KDEL plasmid were subjected to double restriction enzymes digestion with BamH I and Sac I. Thereafter, the digested PCR products and pET24a-2a-F2-KDEL plasmid were purified, respectively, followed by ligation to clone the PCR product into pET24a-2a-F2-KDEL to form pET24a-PE-2a-F2-KDEL. Then, the construct pET24a-PE-2a-F2-KDEL was transformed into host cells (*E. coli*) to carry out mass replication. The replicate PCR products were further confirmed by sequencing. The antigenic fusion protein PE-2a-F2-KDEL has amino acid sequence of SEQ ID NO: 41, and the DNA sequence encoding the fusion protein is SEQ ID NO: 40.

4. PE-2a-F2-KDEL Protein Expression

*E. coli* containing pET24a-PE-2a-F2-KEDL plasmid was incubated in LB medium. The bacterial culture was induced by addition of IPTG to express the antigenic fusion protein PE-2a-F2-KEDL (SEQ ID NO: 41). Methods for protein expression and extraction are described in Example 1.

Example 4

Analysis of PCV2 ORF2 Sequences of Different Subgroups

In addition to subgroup 2a, there are other subgroups of PCV2 virus. Analyses of arginine numbers of amino acid sequences encoded by nucleotides 1-234 at the 5' end of PCV2 ORF2 and amino acid sequences encoded by the DNA sequences from nucleotide 235 to the last nucleotide of PCV2 ORF2 of PCV2 subgroups 2b, 2c, 2d, and 2e are shown as follows, respectively.

PCV2 ORF2 gene sequences provided by Wang et al. (Wang et al., Virus Research 2009, Genetic variation analysis of Chinese strains of porcine circovirus type 2.) are used as standard sequences for phylogenetic analysis of SEQ ID NO: 15 and SEQ ID NO: 19. The result shows that PCV2 ORF2 sequences SEQ ID NO: 15 and SEQ ID NO: 19 belong to PCV2 2b subgroup and PCV2 2d subgroup, respectively (as shown in FIG. 1). In addition, PCV2 ORF2 sequences SEQ ID NO: 50 and SEQ ID NO: 52 serve as a standard strain of PCV2 2c subgroup and PCV2 2e subgroup, respectively.

Results of sequence analysis of PCV2 2b subgroup are shown in Table 3. The ORF2 fragment of PCV2 2b subgroup (2b-ORF2) has the nucleotide sequence of SEQ ID NO: 15 and the amino acid sequence of SEQ ID NO: 16. There are 21 arginine residues in the amino acid sequences encoded by nucleotides 1-234 at the 5' end of 2b-ORF2, whereas there are 10 arginine residues in the amino acid sequences (SEQ ID NO: 18) encoded by nucleotides 235-699 (without the stop codon, SEQ ID NO: 17) of 2b-ORF2. Results of sequence analysis of PCV2 2b subgroup are consistent with that of PCV2 2a subgroup. The arginine numbers at the N terminus of both ORF2 proteins are two times or more than the arginine numbers of the rest part of the ORF2 proteins (as shown in Tables 2 and 3).

TABLE 3

Analysis of Arginine Numbers of the PCV2 2b-ORF2 Amino Acid Sequence

| Subgroup PCV2-2b - nucleotides 1-234 | | | Subgroup PCV2-2b - nucleotides 235-699 | | |
|---|---|---|---|---|---|
| Codon | Amino Acid | Amount | Codon | Amino Acid | Amount |
| AGA | Arginine | 5 | AGA | Arginine | 5 |
| AGG | Arginine | 3 | AGG | Arginine | 1 |
| CGA | Arginine | 1 | CGA | Arginine | 0 |
| CGC | Arginine | 9 | CGC | Arginine | 3 |
| CGG | Arginine | 1 | CGG | Arginine | 0 |
| CGT | Arginine | 2 | CGT | Arginine | 1 |
| Total | | 21 | Total | | 10 |

Results of sequence analysis of PCV2 2c subgroup are shown in Table 4. The ORF2 fragment of PCV2 2c subgroup (2c-ORF2) has the nucleotide sequence of SEQ ID NO: 50 and the amino acid sequence of SEQ ID NO: 51. There are 20 arginine residues in the amino acid sequences encoded by nucleotides 1-234 at the 5' end of 2c-ORF2, whereas there are 10 arginine residues in the amino acid sequences (SEQ ID NO: 55) encoded by nucleotides 235-702 (SEQ ID NO: 54) of 2c-ORF2. Results of sequence analysis of PCV2 2c subgroup are consistent with that of PCV2 2a subgroup and PCV2 2b subgroup. The arginine numbers at the N terminus of all the three ORF2 proteins are two times or more than the arginine numbers of the rest part of the ORF2 proteins (as shown in Tables 2, 3 and 4).

TABLE 4

Analysis of Arginine Numbers of the PCV2 2c-ORF2 Amino Acid Sequence

| Subgroup PCV2-2c - nucleotides 1-234 | | | Subgroup PCV2-2c - nucleotides 235-702 | | |
|---|---|---|---|---|---|
| Codon | Amino Acid | Amount | Codon | Amino Acid | Amount |
| AGA | Arginine | 5 | AGA | Arginine | 6 |
| AGG | Arginine | 3 | AGG | Arginine | 1 |
| CGA | Arginine | 0 | CGA | Arginine | 0 |
| CGC | Arginine | 9 | CGC | Arginine | 2 |
| CGG | Arginine | 1 | CGG | Arginine | 0 |
| CGT | Arginine | 2 | CGT | Arginine | 1 |
| Total | | 20 | Total | | 10 |

Results of sequence analysis of PCV2 2d subgroup are shown in Table 5. The ORF2 fragment of PCV2 2d subgroup (2d-ORF2) has the nucleotide sequence of SEQ ID NO: 19 and the amino acid sequence of SEQ ID NO: 20. There are 21 arginine residues in the amino acid sequences encoded by nucleotides 1-234 at the 5' end of 2d-ORF2, whereas there are 10 arginine residues in the amino acid sequences (SEQ ID NO: 21) encoded by nucleotides 235-702 (without the stop codon, SEQ ID NO: 22) of 2d-ORF2. Results of sequence analysis of PCV2 2d subgroup are consistent with that of PCV2 2a subgroup, PCV2 2b subgroup, and PCV2 2c subgroup. The arginine numbers at the N terminus of all the four ORF2 proteins are two times or more than the arginine numbers of the rest part of the ORF2 proteins (as shown in Tables 2, 3, 4, and 5).

TABLE 5

Analysis of Arginine Numbers of the PCV2 2d-ORF2 Amino Acid Sequence

| Subgroup PCV2-2d - nucleotides 1-234 | | | Subgroup PCV2-2d - nucleotides 235-702 | | |
|---|---|---|---|---|---|
| Codon | Amino Acid | Amount | Codon | Amino Acid | Amount |
| AGA | Arginine | 5 | AGA | Arginine | 4 |
| AGG | Arginine | 3 | AGG | Arginine | 3 |
| CGA | Arginine | 1 | CGA | Arginine | 0 |
| CGC | Arginine | 10 | CGC | Arginine | 1 |
| CGG | Arginine | 0 | CGG | Arginine | 1 |
| CGT | Arginine | 2 | CGT | Arginine | 1 |
| Total | | 21 | Total | | 10 |

Results of sequence analysis of PCV2 2e subgroup are shown in Table 6. The ORF2 fragment of PCV2 2e subgroup (2e-ORF2) has the nucleotide sequence of SEQ ID NO: 52 and the amino acid sequence of SEQ ID NO: 53. There are 20 arginine residues in the amino acid sequences encoded by nucleotides 1-234 at the 5' end of 2e-ORF2, whereas there are 9 arginine residues in the amino acid sequences (SEQ ID NO: 57) encoded by nucleotides 235-699 (without the stop codon, SEQ ID NO: 56) of 2e-ORF2. Results of sequence analysis of PCV2 2e subgroup are consistent with that of PCV2 2a subgroup, PCV2 2b subgroup, PCV2 2c subgroup, and PCV2 2d subgroup. The arginine numbers at the N terminus of all the five ORF2 proteins are two times or more than the arginine numbers of the rest part of the ORF2 proteins (as shown in Tables 2, 3, 4, 5, and 6).

TABLE 6

Analysis of Arginine Numbers of the PCV2 2e-ORF2 Amino Acid Sequence

| Subgroup PCV2-2e - nucleotides 1-234 | | | Subgroup PCV2-2e - nucleotides 235-699 | | |
|---|---|---|---|---|---|
| Codon | Amino Acid | Amount | Codon | Amino Acid | Amount |
| AGA | Arginine | 5 | AGA | Arginine | 4 |
| AGG | Arginine | 3 | AGG | Arginine | 2 |
| CGA | Arginine | 0 | CGA | Arginine | 0 |
| CGC | Arginine | 9 | CGC | Arginine | 2 |
| CGG | Arginine | 1 | CGG | Arginine | 0 |
| CGT | Arginine | 2 | CGT | Arginine | 1 |
| Total | | 20 | Total | | 9 |

Protein expression levels of the arginine-rich domains and the non-arginine-rich domains of PCV2 2b subgroup, PCV2 2c subgroup, PCV2 2d subgroup, and PCV2 2e subgroup are also analyzed by the method described in Example 1. The results are consistent with the results in Example 1. Protein expression level of the arginine-rich domains at N terminus is low, whereas protein expression level of the non-arginine-rich domain is high. Furthermore, analysis of addition or deletion of the arginine shows that deletion of the excessive arginine can increase protein expression of PCV2 ORF2, which is also consistent with the results of PCV2 2a subgroup.

The arginine-rich domain has an amino acid sequence of about residues 1-78 at the N terminus of the full-length peptide of PCV2 ORF2, and the non-arginine-rich domain has an amino acid sequence about from residue 79 to the last residue at C terminus.

Example 5

Construction and Expression of Antigenic Peptides of PCV2 2b Subunit Vaccine

1. Construction and Expression of pET24a-2b-F2

In this example, ORF2 gene of PCV2 2b subgroup in Example 4 was used in construction of the antigenic peptide of PCV2 subunit vaccine. As described in Examples 1 and 3, F2 fragment (nucleotides 235-468 at the 5' end of the full-length DNA sequence of PCV2 2b ORF2 gene, 2b-F2 fragment) is cloned into expression vector. The 2b-F2 fragment of PCV2 2b subgroup has the nucleotide sequence of SEQ ID NO: 17 and the amino acid sequence of SEQ ID NO: 18. The nucleotide sequence of the 2b-F2 fragment was amplified by PCR. The PCR primers are shown as follows.

```
Forward primer pF-2b
(with a Sac I restriction site):
                                  (SEQ ID NO: 42)
5'-C GAGCTC TTTCTTCCCCCAGGAGGGGGC-3'
Sac I Reverse primer pR-2b
(with a Hind III restriction site):
                                  (SEQ ID NO: 43)
5'-CCC AAGCTT GTAGGAGAAGGGCTGGGTTAT-3'
Hind III
```

Conditions for PCR reaction comprises: 95° C. for 5 minutes, 25 cycles of 95° C. for 30 seconds, 55° C. for 30 seconds, and 72° C. for 30 seconds, and 72° C. for 5 minutes for elongation. PCR product and pET24a expression vector (Novagen) were subjected to double restriction enzymes digestion with Sac I and Hind III. Thereafter, the digested PCR products and pET24a expression vector were purified, respectively, followed by ligation to clone the PCR product into pET24a expression vector to form pET24a-2b-F2 plasmid. Then, the construct was transformed into host cells (*E. coli*) to carry out mass replication. The replicate PCR products were further confirmed by sequencing. *E. coli* containing pET24a-2b-F2 μlasmid was incubated in LB medium. The bacterial culture was induced by addition of IPTG to express the antigenic protein 2b-F2 (SEQ ID NO: 18). Methods for protein expression and extraction are described in Example 1.

2. Construction and Expression of pET24a-PE-2b-F2-KDEL

In addition to using 2b-F2 peptide as the antigenic peptide of PCV2 subunit vaccine, in this Example, PE protein and KDEL signal peptide were fused with the 2b-F2 peptide at the N and C terminuses, respectively, to produce PE-2b-F2-KDEL recombinant fusion protein to induce sufficient immunity against PCV2 infection in animals.

PE-2b-F2-KDEL recombinant fusion protein has a DNA sequence of SEQ ID NO: 44 and an amino acid sequence of SEQ ID NO: 45. The strategy for construction of plasmid expressing PE-2b-F2-KDEL recombinant fusion protein (pET24a-PE-2b-F2-KDEL) is the same as the strategy described in Example 3. First, DNA sequence (SEQ ID NO: 30) encoding KDEL signal peptide was cloned into pET24a vector to form pET24a-KDEL plasmid. Method for construction of pET24a-KDEL plasmid is described in Example 3. After that, DNA sequence (SEQ ID NO: 17) of the 2b-F2 fragment was cloned into pET24a-KDEL plasmid to form pET24a-2b-F2-KDEL plasmid. Finally, DNA sequence (SEQ ID NO: 34) encoding PE protein was cloned into pET24a-2b-F2-KDEL plasmid to form pET24a-PE-2b-F2-KDEL plasmid. Method for construction of pET24a-PE-2b-F2-KDEL plasmid is described in Example 3. Then, *E. coli* containing pET24a-PE-2b-F2-KDEL plasmid was incubated in LB medium. The bacterial culture was induced by addition of IPTG to express PE-2b-F2-KDEL recombinant protein (SEQ ID NO: 45). Methods for protein expression and extraction are described in Example 1.

Example 6

Construction and Expression of Antigenic Peptides of PCV2 2d Subunit Vaccine

1. Construction and Expression of pET24a-2d-F2

In this example, ORF2 gene of PCV2 2d subgroup in Example 4 was used in construction of the antigenic peptide of PCV2 subunit vaccine. As described in Examples 1 and 3, F2 fragment (nucleotides 235-468 at the 5' end of the full-length DNA sequence of PCV2 2d ORF2 gene, 2d-F2 fragment) is cloned into expression vector. The 2d-F2 fragment of PCV2 2d subgroup has the nucleotide sequence of SEQ ID NO: 21 and the amino acid sequence of SEQ ID NO: 22. The nucleotide sequence of the 2d-F2 fragment was amplified by PCR. The PCR primers are shown as follows.

```
Forward primer pF-2d
(with a Sac I restriction site):
                              (SEQ ID NO: 46)
5'-C GAGCTC TTTCTTCCCCCAGGAGGGGGC-3'
Sac I Reverse primer pR-2d
(with a Hind III restriction site):
```

```
                              (SEQ ID NO: 47)
5'-CCC AAGCTT GTAGGAGAAGGGCTGGGTTAT-3'
Hind III
```

Conditions for PCR reaction comprises: 95° C. for 5 minutes, 25 cycles of 95° C. for 30 seconds, 55° C. for 30 seconds, and 72° C. for 30 seconds, and 72° C. for 5 minutes for elongation. PCR product and pET24a expression vector (Novagen) were subjected to double restriction enzymes digestion with Sac I and Hind III. Thereafter, the digested PCR products and pET24a expression vector were purified, respectively, followed by ligation to clone the PCR product into pET24a expression vector to form pET24a-2d-F2 plasmid. Then, the construct was transformed into host cells (*E. coli*) to carry out mass replication. The replicate PCR products were further confirmed by sequencing. *E. coli* containing pET24a-2d-F2 μlasmid was incubated in LB medium. The bacterial culture was induced by addition of IPTG to express the antigenic protein 2d-F2 (SEQ ID NO: 22). Methods for protein expression and extraction are described in Example 1.

2. Construction and Expression of pET24a-PE-2d-F2-KDEL

In addition to using 2d-F2 peptide as the antigenic peptide of PCV2 subunit vaccine, in this Example, PE protein and KDEL signal peptide were fused with the 2d-F2 peptide at the N and C terminuses, respectively, to produce PE-2d-F2-KDEL recombinant fusion protein to induce sufficient immunity against PCV2 infection in animals.

PE-2d-F2-KDEL recombinant fusion protein has a DNA sequence of SEQ ID NO: 48 and an amino acid sequence of SEQ ID NO: 49. The strategy for construction of plasmid expressing PE-2d-F2-KDEL recombinant fusion protein (pET24a-PE-2d-F2-KDEL) is the same as the strategy described in Example 3. First, DNA sequence (SEQ ID NO: 30) encoding KDEL signal peptide was cloned into pET24a vector to form pET24a-KDEL plasmid. Method for construction of pET24a-KDEL plasmid is described in Example 3. After that, DNA sequence (SEQ ID NO: 21) of the 2d-F2 fragment was cloned into pET24a-KDEL plasmid to form pET24a-2d-F2-KDEL plasmid. Finally, DNA sequence (SEQ ID NO: 34) encoding PE protein was cloned into pET24a-2d-F2-KDEL plasmid to form pET24a-PE-2d-F2-KDEL plasmid. Method for construction of pET24a-PE-2d-F2-KDEL plasmid is described in Example 3. Then, *E. coli* containing pET24a-PE-2d-F2-KDEL plasmid was incubated in LB medium. The bacterial culture was induced by addition of IPTG to express PE-2d-F2-KDEL recombinant protein (SEQ ID NO: 49). Methods for protein expression and extraction are described in Example 1.

Example 7

Immunogenicity Analysis of Antigenic Peptides of PCV2 Subunit Vaccine-1

1. Immunization of Mice

PCV2 subunit vaccine was made with the 2a-F2 recombinant protein (SEQ ID NO: 6) prepared in Example 1 and the PE-2a-F2-KDEL recombinant protein (SEQ ID NO: 41) prepared in Example 3, respectively, and Freund's complete adjuvant. Mice were vaccinated with the PCV2 subunit vaccine to analyze immunogenicity of the antigenic peptides of the PCV2 subunit vaccine.

Five- to six-week-old healthy SPF mice were randomly divided into 3 groups of 3 mice each. Enzyme-linked immunosorbent assay (ELISA) showed that all the 9 mice were negative for anti-PCV2 antibodies. Each mouse in the 2 vaccine groups (Groups 1 and 2) was injected intraperitoneally with 100 µg of recombinant protein. Mice in Group 3 were injected with PBS and served as negative control. Two weeks after primary immunization (p.i.), the mice in the 2 vaccine groups were boosted with the same dose of the 2 different recombinant proteins, respectively. Serum samples were collected at weeks 2, 4, 5, and 8 post-primary immunization. All the serum samples were tested by ELISA to measure the titer of anti-PCV2 antibodies.

2. Detection of Anti-PCV2 Antibodies by ELISA

Ninety-six well plates containing PCV2 pathogen antigen (300 ng/well) were used as the ELISA plates in this example. The ELISA plates were washed 3 times with 50 mmol/L PBS (pH 7.2) containing 500 µl/L Tween-20 (i.e. PBST) for 3 to 5 minutes each time. To block the ELISA plates, 2004 of 0.15% BSA blocking solution was added to each well of the ELISA plates, and then the ELISA plates were incubated for 2 hours at 37° C. After that, the ELISA plates were washed with PBS. Mice serum samples were diluted fifty-fold (1:50) with PBS and then diluted two-fold serially. Each sample had 8 repeats. Diluted serum samples were added to the wells of the ELISA plates (100 µl/well), and the plates were incubated for 1 hour at 37° C. After incubation, the plates were washed with PBS. Anti-mouse IgG antibody conjugated with alkaline phosphatase (AP) was then added to the wells. After incubating for 1 hour at 37° C., the plates were washed with PBS. For visualization of results, para-Nitrophenylphosphate (pNPP) was added to the wells. Following incubation, the reaction was stopped by adding 1M NaOH. The optical density of each well was read using optical density at 405 nm. Each sample was analyzed in duplicate, and the O.D. values of duplicates were averaged.

Figure 6:
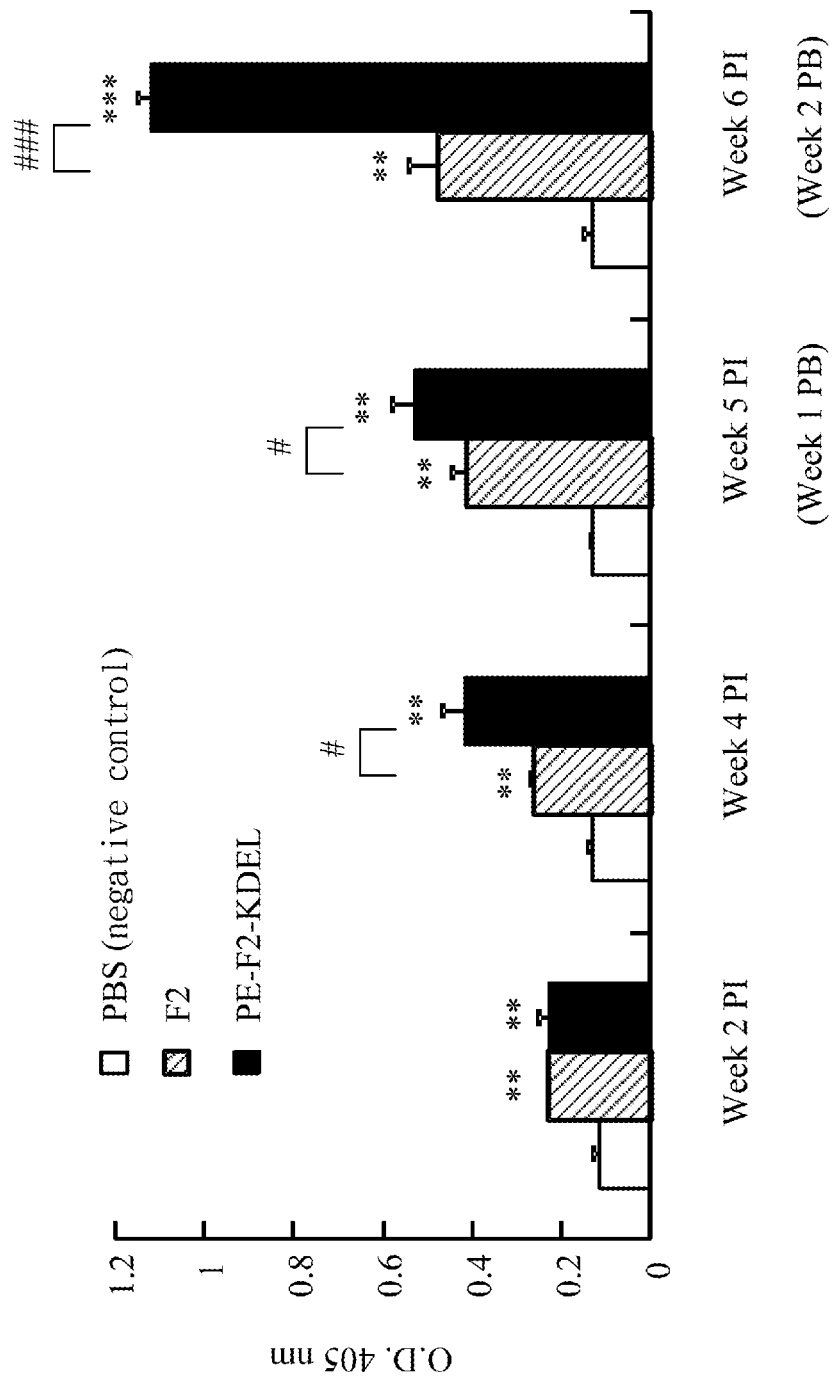
FIG. 6 illustrates the results of PCV2 ELISA of serum samples collected at different time points from mice vaccinated with recombinant proteins of the 2a-F2 fragment and recombinant proteins of the PE-2a-F2-KDEL fragment, respectively. *, $p<0.05$; , $p<0.01$; *, $p<0.001$; #, $p<0.05$; ##, $p<0.01$; ###, $p<0.001$. (PI: post-immunization; PB: post-booster)

ELISA results are shown in FIG. 6. The PE-2a-F2-KDEL recombinant protein (SEQ ID NO: 41) induces higher level of serum antibodies against PCV2 in tested animals than the 2a-F2 recombinant protein (SEQ ID NO: 6) does. There are significant differences between the levels of serum antibodies against PCV2 in Group 1 and Group 2 at week 4 post-primary immunization ($p<0.05$). The differences between the levels of serum antibodies against PCV2 in Group 1 and Group 2 are more significant at week 6 post-primary immunization ($p<0.01$). Additionally, compared to the antibody level of negative control, the antibody levels of Group 1 and Group 2 are significantly higher ($p<0.01$).

Example 8

Immunogenicity Analysis of Antigenic Peptides of PCV2 Subunit Vaccine-2

1. Immunization of Mice

In this Example, immunogenicity of PE-2a-F2-KDEL recombinant protein disclosed herein in tested animals is compared with immunogenicity of PCV2 whole virus in tested animals.

PCV2 subunit vaccine was made with the PE-2a-F2-KDEL recombinant protein (SEQ ID NO: 41) prepared in Example 3 and oil adjuvant Montanide ISA 206 (Seppic, France). In addition, PCV2 whole virus vaccine was made with in activated PCV2 whole virus ($10^6$ $TCID_{50}$/ml) and oil adjuvant Montanide ISA 206 (Seppic, France). There are 100 µl inactivated PCV2 whole virus and 250 µl adjuvant in a single dose of PCV2 whole virus vaccine. The two vaccines were used to vaccinate mice.

Five- to six-week-old healthy SPF mice were randomly divided into 3 groups of 5 mice each. Enzyme-linked immunosorbent assay (ELISA) showed that all the 15 mice were negative for anti-PCV2 antibodies. Each mouse in Groups 1 was injected intraperitoneally with 100 µg of recombinant protein. Each mouse in Groups 2 was injected intraperitoneally with a single dose of PCV2 whole virus vaccine. Mice in Group 3 were injected with oil adjuvant Montanide ISA 206 and served as negative control. Three weeks after primary immunization (p.i.), the mice in the 2 vaccine groups were boosted with the same dose of the 2 different vaccines, respectively. Serum samples were collected at weeks 0, 1, 2, 3, 4, and 5 post-primary immunization. All the serum samples were tested by ELISA to measure the titer of anti-PCV2 antibodies.

2. Detection of Anti-PCV2 Antibodies by ELISA

Figure 7:
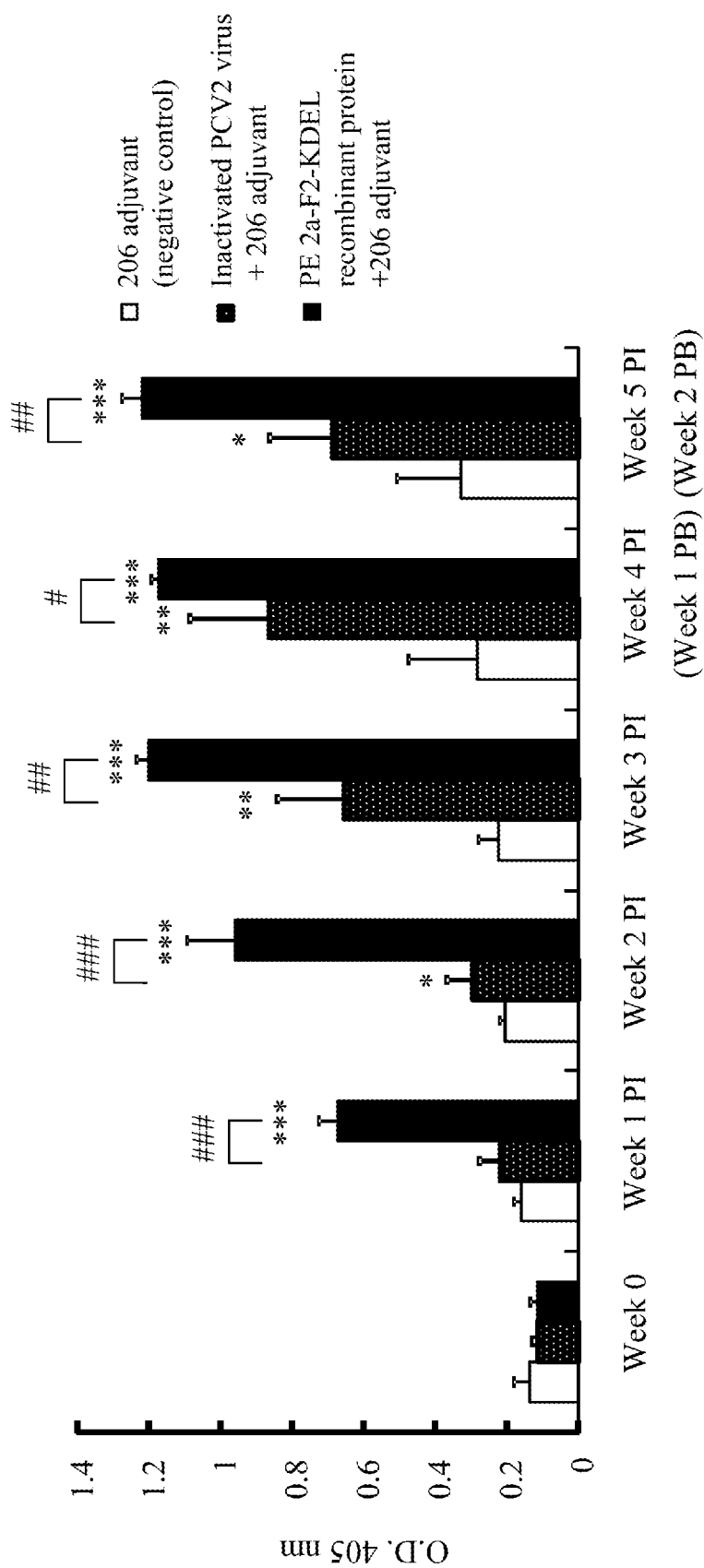
FIG. 7 shows the results of PCV2 ELISA of serum samples collected at different time points from mice vaccinated with recombinant proteins of the PE-2a-F2-KDEL fragment and PCV2 whole virus vaccine, respectively. *, $p<0.05$; , $p<0.01$; *, $p<0.001$; #, $p<0.05$; ##, $p<0.01$; ###, $p<0.001$. (PI: post-immunization; PB: post-booster)

ELISA method for detection of anti-PCV2 antibodies is described in Example 7. ELISA results are shown in FIG. 7. The PE-2a-F2-KDEL recombinant protein (SEQ ID NO: 41) induces higher level of serum antibodies against PCV2 in tested animals than the inactivated PCV2 whole virus antigen does. There are significant differences between the levels of serum antibodies against PCV2 in Group 1 and Group 2 at week 1 post-primary immunization ($p<0.001$). Additionally, compared to the antibody level of negative control, the antibody level of mice vaccinated with the PE-2a-F2-KDEL recombinant protein (Group 1) is significantly higher ($p<0.001$).

Furthermore, pigs were vaccinated with the 2a-F2 and PE-2a-F2-KDEL recombinant proteins, respectively, and both of the recombinant proteins were able to induce serum antibodies against PCV2 in pigs. In addition, the vaccinated pigs were challenged with PCV2 virus to evaluate the efficacy of the recombinant proteins. First, the recombinant proteins were formulated as subunit vaccine and injected into pigs. Then, the pigs were challenged with PCV2 virus. The results show that the protection rates of immunization groups are higher then that of the negative control (no vaccination). The protection rates used herein include a decrease in viremia and alleviation of PCV2 symptoms. Therefore, the results show that the PCV2 subunit vaccine prepared with the recombinant proteins can effectively induce immunity in animals and increase survival rate of the animals.

Additionally, ORF2 proteins or fragments thereof of PCV2 2b subgroup, PCV2 2c subgroup, PCV2 2d subgroup, and PCV2 2e subgroup were prepared by the methods described in Examples 1-3, respectively, and immunogenicity of the ORF2 proteins or fragments thereof were analyzed by the methods described in Examples 7 and 8. The results show that the ORF2 fragments of these PCV2 subgroups (for example, F2 fragment) and recombinant fusion proteins thereof (for example, PE-F2-KDEL) can induce immunity in animals (such as pigs) and prevent the animals from PCV2 infection.

The PCV2 subunit vaccine provided in the disclosure has the following advantages comparing with other conventional techniques.

The PCV2 subunit vaccine provided in the disclosure is prepared by genetic engineering, in which PCV2 ORF2 protein fragments that can be highly expressed in biological expression systems are cloned and used as antigenic peptides of the subunit vaccine. The subunit vaccine can induce sufficient immunity against PCV2 infection in animals, and the PCV2 ORF2 protein fragments can be mass-produced by genetic engineering to reduce cost of manufacturing the vaccine.

Another PCV2 subunit vaccine provided in the disclosure contains a PE-F2-KDEL antigenic fusion protein, which is a recombinant protein of F2 peptide of PCV2 ORF2, PE protein, and KDEL signal peptide. Animal trials show that this PCV2 subunit vaccine can efficiently induce higher immunity against PCV2 infection in animals.

The subunit vaccine provided in the disclosure is developed by genetic engineering, and the vaccine has the advantages of simple production process, low cost, high purity, high yield, and good safety.

Many changes and modifications in the above-described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A porcine circovirus type 2 (PCV2) immunogenic composition, comprising an antigenic peptide, wherein the antigenic peptide consists of at least one of:

(a) at least one recombinant peptide fragment of a PCV2 open reading frame 2 (ORF2) selected from the group consisting of a recombinant peptide consisting of amino acids 79-156 at the N-terminus of a PCV2 ORF2 of SEQ ID NO: 2, a recombinant peptide consisting of amino acids 157-233 at the N-terminus of the PCV2 ORF2 of SEQ ID NO: 2, a recombinant peptide consisting of amino acids 117-233 at the N-terminus of the PCV2 ORF2 of SEQ ID NO: 2, a recombinant peptide consisting of amino acids 79-233 at the N-terminus of the PCV2 ORF2 of SEQ ID NO: 2, a recombinant peptide consisting of amino acids 79-156 at the N-terminus of a PCV2 ORF2 of SEQ ID NO: 16, a recombinant peptide consisting of amino acids 157-233 at the N-terminus of the PCV2 ORF2 of SEQ ID NO: 16, a recombinant peptide consisting of amino acids 117-233 at the N-terminus of the PCV2 ORF2 of SEQ ID NO: 16, a recombinant peptide consisting of amino acids 79-233 at the N-terminus of the PCV2 ORF2 of SEQ ID NO: 16, a recombinant peptide consisting of amino acids 79-156 at the N-terminus of a PCV2 ORF2 of SEQ ID NO: 20, a recombinant peptide consisting of amino acids 157-233 at the N-terminus of the PCV2 ORF2 of SEQ ID NO: 20, a recombinant peptide consisting of amino acids 117-233 at the N-terminus of the PCV2 ORF2 of SEQ ID NO: 20, a recombinant peptide consisting of amino acids 79-233 at the N-terminus of the PCV2 ORF2 of SEQ ID NO: 20, a recombinant peptide consisting of amino acids 79-156 at the N-terminus of a PCV2 ORF2 of SEQ ID NO: 51, a recombinant peptide consisting of amino acids 157-233 at the N-terminus of the PCV2 ORF2 of SEQ ID NO: 51, a recombinant peptide consisting of amino acids 117-233 at the N-terminus of the PCV2 ORF2 of SEQ ID NO: 51, a recombinant peptide consisting of amino acids 79-233 at the N-terminus of the PCV2 ORF2 of SEQ ID NO: 51, a recombinant peptide consisting of amino acids 79-156 at the N-terminus of a PCV2 ORF2 of SEQ ID NO: 53, a recombinant peptide consisting of amino acids 157-233 at the N-terminus of the PCV2 ORF2 of SEQ ID NO: 53, a recombinant peptide consisting of amino acids 117-233 at the N-terminus of the PCV2 ORF2 of SEQ ID NO: 53, and a recombinant peptide consisting of amino acids 79-233 at the N-terminus of the PCV2 ORF2 of SEQ ID NO: 53; and (b) a recombinant fusion protein comprising, from the amino-terminus to the carboxyl-terminus of the recombinant fusion protein: a *Pseudomonas aeruginosa* exotoxin A (PE) peptide having the sequence of SEQ ID NO: 35; a PCV2 ORF2 protein sequence consisting of at least one of the recombinant peptide fragments of the PCV2 ORF2 of (a); and a KDEL signal peptide having the sequence of SEQ ID NO: 31; and wherein the immunogenic composition does not include a peptide fragment consisting of amino acids 1-78 at the N-terminus of the PCV2 ORF2.

2. The PCV2 immunogenic composition of claim 1, further comprising open reading frames (ORFs) other than ORF 2 of the PCV2, wherein the ORFs other than ORF2 comprise ORF1 and ORF3.

3. The PCV2 immunogenic composition of claim 1, further comprising at least one pathogen antigen selected from the group consisting of an antigen of swine influenza virus (SIV), an antigen of porcine reproductive and respiratory syndrome virus (PRRSV), an antigen of mycoplasma, antigen of porcine parvovirus (PPV), an antigen of erysipelas, and an antigen of pseudorabies virus.

4. The PCV2 immunogenic composition of claim 1, wherein the peptide fragment of the PCV2 ORF2 of (a) is selected from the group consisting of SEQ ID NO: 6, SEQ ID NO: 8, SEQ ID NO: 10, SEQ ID NO: 12, SEQ ID NO: 18, SEQ ID NO: 22, SEQ ID NO: 55, and SEQ ID NO: 57.

5. The PCV2 immunogenic composition of claim 1, further comprising at least one agent selected from the group consisting of vehicles, solvent, emulsifier, suspending agents, decomposer, binding agents, excipient, stabilizing agents, chelating agents, diluent, gelling agents, preservatives, lubricant, surfactant, adjuvant, and biological carriers.

6. The PCV2 immunogenic composition of claim 1, wherein the recombinant fusion protein of (b) is selected from the group consisting of SEQ ID NO: 41, SEQ ID NO: 45, and SEQ ID NO: 49.

* * * * *

SEQUENCE LISTING

<160> NUMBER OF SEQ ID NOS: 57

<210> SEQ ID NO 1
<211> LENGTH: 699
<212> TYPE: DNA
<213> ORGANISM: Porcine circovirus

<400> SEQUENCE: 1

```
atgacgtatc caaggaggcg tttccgcaga cgaagacacc gcccccgcag ccatcttggc      60
cagatcctcc gccgccgccc ctggctcgtc cacccccgcc accgttaccg ctggagaagg     120
aaaaatggca tcttcaacac ccgcctctcc cgcaccttcg gatatactgt caaggctagc     180
acagtcagaa cgccctcctg ggcggtggac atgatgagat taatattaa cgactttgtt     240 cccccgggag gggggaccaa caaaatctct ataccctttg aatactacag aataagaaag     300
gttaaggttg aattctggcc ctgctcccca atcacccagg gtgacagggg agtgggctcc     360
actgctgtta ttctagatga taactttgta actaaggcca cagccctaac ctatgacccc     420
tatgtaaact actcctcccg ccatacaatc ccccaacct tctcctacca ctcccggtac     480
tttaccccaa aacctgtcct tgattccact attgattact tccaaccaaa cagcaaaagg     540
aatcagattt ggctgaggct acaaacctcg gcaaatgtgg accacgtagg cctcggtact     600
gcgttcgaaa acagtaaata cgaccaggac tacaatatcc gtgtaactat gtatgtacaa     660
ttcagagaat ttaatcttaa agacccccca cttaaaccc                            699
```

<210> SEQ ID NO 2
<211> LENGTH: 233
<212> TYPE: PRT
<213> ORGANISM: Porcine circovirus

<400> SEQUENCE: 2

```
Met Thr Tyr Pro Arg Arg Arg Phe Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Ser Thr Val Arg Thr
    50                  55                  60

Pro Ser Trp Ala Val Asp Met Met Arg Phe Asn Ile Asn Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125
```

```
Phe Val Thr Lys Ala Thr Ala Leu Thr Tyr Asp Pro Tyr Val Asn Tyr
        130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Ser Lys Arg Asn Gln Ile Trp Leu Arg Leu Gln Thr Ser Ala Asn
                180                 185                 190

Val Asp His Val Gly Leu Gly Thr Ala Phe Glu Asn Ser Lys Tyr Asp
            195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230
```

<210> SEQ ID NO 3
<211> LENGTH: 234
<212> TYPE: DNA
<213> ORGANISM: Porcine circovirus

<400> SEQUENCE: 3

```
atgacgtatc caaggaggcg tttccgcaga cgaagacacc gcccccgcag ccatcttggc    60
cagatcctcc gccgccgccc ctggctcgtc caccccgcc accgttaccg ctggagaagg    120
aaaaatggca tcttcaacac ccgcctctcc cgcaccttcg gatatactgt caaggctagc   180
acagtcagaa cgccctcctg gcggtggac atgatgagat taatattaa cgac            234
```

<210> SEQ ID NO 4
<211> LENGTH: 78
<212> TYPE: PRT
<213> ORGANISM: Porcine circovirus

<400> SEQUENCE: 4

```
Met Thr Tyr Pro Arg Arg Arg Phe Arg Arg Arg His Arg Pro Arg
1               5                   10                  15

Ser His Leu Gly Gln Ile Leu Arg Arg Arg Pro Trp Leu Val His Pro
                20                  25                  30

Arg His Arg Tyr Arg Trp Arg Arg Lys Asn Gly Ile Phe Asn Thr Arg
            35                  40                  45

Leu Ser Arg Thr Phe Gly Tyr Thr Val Lys Ala Ser Thr Val Arg Thr
        50                  55                  60

Pro Ser Trp Ala Val Asp Met Met Arg Phe Asn Ile Asn Asp
65                  70                  75
```

<210> SEQ ID NO 5
<211> LENGTH: 234
<212> TYPE: DNA
<213> ORGANISM: Porcine circovirus

<400> SEQUENCE: 5

```
tttgttcccc cgggaggggg gaccaacaaa atctctatac cctttgaata ctacagaata    60
agaaaggtta aggttgaatt ctggccctgc tccccaatca cccagggtga caggggagtg   120
ggctccactg ctgttattct agatgataac tttgtaacta aggccacagc cctaacctat   180 gaccccctatg taaactactc ctcccgccat acaatccccc aaccttctc ctac         234
```

<210> SEQ ID NO 6
<211> LENGTH: 78

<212> TYPE: PRT
<213> ORGANISM: Porcine circovirus

<400> SEQUENCE: 6

```
Phe Val Pro Pro Gly Gly Thr Asn Lys Ile Ser Ile Pro Phe Glu
1               5                  10                  15

Tyr Tyr Arg Ile Arg Lys Val Lys Val Glu Phe Trp Pro Cys Ser Pro
            20                  25                  30

Ile Thr Gln Gly Asp Arg Gly Val Gly Ser Thr Ala Val Ile Leu Asp
        35                  40                  45

Asp Asn Phe Val Thr Lys Ala Thr Ala Leu Thr Tyr Asp Pro Tyr Val
    50                  55                  60

Asn Tyr Ser Ser Arg His Thr Ile Pro Gln Pro Phe Ser Tyr
65                  70                  75
```

<210> SEQ ID NO 7
<211> LENGTH: 231
<212> TYPE: DNA
<213> ORGANISM: Porcine circovirus

<400> SEQUENCE: 7

```
cactcccggt actttacccc aaaacctgtc cttgattcca ctattgatta cttccaacca    60
aacagcaaaa ggaatcagat ttggctgagg ctacaaacct cggcaaatgt ggaccacgta   120
ggcctcggta ctgcgttcga aaacagtaaa tacgaccagg actacaatat ccgtgtaact   180
atgtatgtac aattcagaga atttaatctt aaagaccccc cacttaaacc c            231
```

<210> SEQ ID NO 8
<211> LENGTH: 77
<212> TYPE: PRT
<213> ORGANISM: Porcine circovirus

<400> SEQUENCE: 8

```
His Ser Arg Tyr Phe Thr Pro Lys Pro Val Leu Asp Ser Thr Ile Asp
1               5                  10                  15

Tyr Phe Gln Pro Asn Ser Lys Arg Asn Gln Ile Trp Leu Arg Leu Gln
            20                  25                  30

Thr Ser Ala Asn Val Asp His Val Gly Leu Gly Thr Ala Phe Glu Asn
        35                  40                  45

Ser Lys Tyr Asp Gln Asp Tyr Asn Ile Arg Val Thr Met Tyr Val Gln
    50                  55                  60

Phe Arg Glu Phe Asn Leu Lys Asp Pro Pro Leu Lys Pro
65                  70                  75
```

<210> SEQ ID NO 9
<211> LENGTH: 351
<212> TYPE: DNA
<213> ORGANISM: Porcine circovirus

<400> SEQUENCE: 9

```
ggagtgggct ccactgctgt tattctagat gataactttg taactaaggc cacagcccta    60
acctatgacc cctatgtaaa ctactcctcc cgccatacaa tcccccaacc cttctcctac   120
cactcccggt actttacccc aaaacctgtc cttgattcca ctattgatta cttccaacca   180
aacagcaaaa ggaatcagat ttggctgagg ctacaaacct cggcaaatgt ggaccacgta   240
ggcctcggta ctgcgttcga aaacagtaaa tacgaccagg actacaatat ccgtgtaact   300
atgtatgtac aattcagaga atttaatctt aaagaccccc cacttaaacc c            351
```

<210> SEQ ID NO 10
<211> LENGTH: 117
<212> TYPE: PRT
<213> ORGANISM: Porcine circovirus

<400> SEQUENCE: 10

Gly Val Gly Ser Thr Ala Val Ile Leu Asp Asp Asn Phe Val Thr Lys
1               5                   10                  15

Ala Thr Ala Leu Thr Tyr Asp Pro Tyr Val Asn Tyr Ser Ser Arg His
            20                  25                  30

Thr Ile Pro Gln Pro Phe Ser Tyr His Ser Arg Tyr Phe Thr Pro Lys
        35                  40                  45

Pro Val Leu Asp Ser Thr Ile Asp Tyr Phe Gln Pro Asn Ser Lys Arg
    50                  55                  60

Asn Gln Ile Trp Leu Arg Leu Gln Thr Ser Ala Asn Val Asp His Val
65                  70                  75                  80

Gly Leu Gly Thr Ala Phe Glu Asn Ser Lys Tyr Asp Gln Asp Tyr Asn
                85                  90                  95

Ile Arg Val Thr Met Tyr Val Gln Phe Arg Glu Phe Asn Leu Lys Asp
            100                 105                 110

Pro Pro Leu Lys Pro
        115

<210> SEQ ID NO 11
<211> LENGTH: 465
<212> TYPE: DNA
<213> ORGANISM: Porcine circovirus

<400> SEQUENCE: 11
tttgttcccc cgggaggggg gaccaacaaa atctctatac cctttgaata ctacagaata      60
agaaaggtta aggttgaatt ctggccctgc tccccaatca cccagggtga caggggagtg     120
ggctccactg ctgttattct agatgataac tttgtaacta aggccacagc cctaaccctat    180 gaccccctatg taaactactc ctcccgccat acaatccccc aacccttctc ctaccactcc    240
cggtacttta ccccaaaacc tgtccttgat tccactattg attacttcca accaaacagc    300
aaaaggaatc agatttggct gaggctacaa acctcggcaa atgtggacca cgtaggcctc    360
ggtactgcgt tcgaaaacag taaatacgac caggactaca atatccgtgt aactatgtat    420
gtacaattca gagaatttaa tcttaaagac cccccactta aaccc                    465

<210> SEQ ID NO 12
<211> LENGTH: 155
<212> TYPE: PRT
<213> ORGANISM: Porcine circovirus

<400> SEQUENCE: 12

Phe Val Pro Pro Gly Gly Gly Thr Asn Lys Ile Ser Ile Pro Phe Glu
1               5

Arg Tyr Phe Thr Pro Lys Pro Val Leu Asp Ser Thr Ile Asp Tyr Phe
                85                  90                  95

Gln Pro Asn Ser Lys Arg Asn Gln Ile Trp Leu Arg Leu Gln Thr Ser
            100                 105                 110

Ala Asn Val Asp His Val Gly Leu Gly Thr Ala Phe Glu Asn Ser Lys
        115                 120                 125

Tyr Asp Gln Asp Tyr Asn Ile Arg Val Thr Met Tyr Val Gln Phe Arg
    130                 135                 140

Glu Phe Asn Leu Lys Asp Pro Pro Leu Lys Pro
145                 150                 155

<210> SEQ ID NO 13
<211> LENGTH: 468
<212> TYPE: DNA
<213> ORGANISM: Porcine circovirus

<400> SEQUENCE: 13
atgacgtatc caaggaggcg tttccgcaga cgaagacacc gcccccgcag ccatcttggc    60
cagatcctcc gccgccgccc ctggctcgtc cacccccgcc accgttaccg ctggagaagg   120
aaaaatggca tcttcaacac ccgcctctcc gcaccttcg gatatactgt caaggctagc    180
acagtcagaa cgccctcctg gcggtggac atgatgagat taatattaa cgactttgtt     240
cccccgggag gggggaccaa caaaatctct atacccttg aatactacag aataagaaag   300
gttaaggttg aattctggcc ctgctcccca atcacccagg gtgacagggg agtgggctcc   360
actgctgtta ttctagatga taactttgta actaaggcca cagccctaac ctatgacccc   420
tatgtaaact actcctcccg ccatacaatc ccccaaccct tctcctac                468

<210> SEQ ID NO 14
<211> LENGTH: 156
<212> TYPE: PRT
<213> ORGANISM: Porcine circovirus

<400> SEQUENCE: 14

Met Thr Tyr Pro Arg Arg Arg Phe Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Ser Thr Val Arg Thr
    50                  55                  60

Pro Ser Trp Ala Val Asp Met Met Arg Phe Asn Ile Asn Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr
145                 150                 155

<210> SEQ ID NO 15

<211> LENGTH: 702
<212> TYPE: DNA
<213> ORGANISM: Porcine circovirus

<400> SEQUENCE: 15

```
atgacgtatc caaggaggcg ttaccggaga agaagacacc gcccccgcag ccatcttgga      60
cagatcctcc gccgccgccc ctggctcgtc caccccgcc accgttaccg ctggagaagg     120
aaaaatggca tcttcaacac ccgcctctcc gcaccttcg gatatactat caagcgaacc     180
acagtcaaaa cgcccctcctg gcggtggac atgatgagat caatattaa tgactttctt     240
cccccaggag ggggctcaaa ccccgctct gtgcccttg aatactacag aataagaaag     300
gttaaggttg aattctggcc ctgctcccg atcacccagg gtgacagggg agtgggctcc     360
agtgctgtta ttctagatga taactttgta acaaaggcca cagccctcac ctatgacccc     420
tatgtaaact actcctcccg ccataccata acccagccct ctcctacca ctcccgctac     480
tttaccccca aacctgtcct agattccact attgattact ccaaccaaa caacaaaaga     540
aatcagctgt ggctgagact acaaactgct ggaaatgtag accacgtagg cctcggcact     600
gcgttcgaaa acagtatata cgaccaggaa tacaatatcc gtgtaaccat gtatgtacaa     660
ttcagagaat taatcttaa agacccccca cttaacccttaa                          702
```

<210> SEQ ID NO 16
<211> LENGTH: 233
<212> TYPE: PRT
<213> ORGANISM: Porcine circovirus

<400> SEQUENCE: 16

```
Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
                20                  25                  30

Arg His Arg Tyr Arg Trp Arg Arg Lys Asn Gly Ile Phe Asn Thr Arg
            35                  40                  45

Leu Ser Arg Thr Phe Gly Tyr Thr Ile Lys Arg Thr Thr Val Lys Thr
        50                  55                  60

Pro Ser Trp Ala Val Asp Met Met Arg Phe Asn Ile Asn Asp Phe Leu
65                  70                  75                  80

Pro Pro Gly Gly Gly Ser Asn Pro Arg Ser Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Ser Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ala Gly Asn
            180                 185                 190

Val Asp His Val Gly Leu Gly Thr Ala Phe Glu Asn Ser Ile Tyr Asp
        195                 200                 205

Gln Glu Tyr Asn Ile Arg Val Thr Met Tyr Val Gln Phe Arg Glu Phe
    210                 215                 220
```

```
Asn Leu Lys Asp Pro Pro Leu Asn Pro
225                 230

<210> SEQ ID NO 17
<211> LENGTH: 234
<212> TYPE: DNA
<213> ORGANISM: Porcine circovirus

<400> SEQUENCE: 17
tttcttcccc caggagggg ctcaaacccc cgctctgtgc cctttgaata ctacagaata      60
agaaaggtta aggttgaatt ctggccctgc tccccgatca cccagggtga caggggagtg    120
ggctccagtg ctgttattct agatgataac tttgtaacaa aggccacagc cctcacctat    180 gaccctatg taaactactc ctcccgccat accataaccc agcccttctc ctac           234

<210> SEQ ID NO 18
<211> LENGTH: 78
<212> TYPE: PRT
<213> ORGANISM: Porcine circovirus

<400> SEQUENCE: 18

Phe Leu Pro Pro Gly Gly Gly Ser Asn Pro Arg Ser Val Pro Phe Glu
1               5                   10                  15

Tyr Tyr Arg Ile Arg Lys Val Lys Val Glu Phe Trp Pro Cys Ser Pro
            20                  25                  30

Ile Thr Gln Gly Asp Arg Gly Val Gly Ser Ser Ala Val Ile Leu Asp
        35                  40                  45

Asp Asn Phe Val Thr Lys Ala Thr Ala Leu Thr Tyr Asp Pro Tyr Val
    50                  55                  60

Asn Tyr Ser Ser Arg His Thr Ile Thr Gln Pro Phe Ser Tyr
65                  70                  75

<210> SEQ ID NO 19
<211> LENGTH: 705
<212> TYPE: DNA
<213> ORGANISM: Porcine circovirus

<400> SEQUENCE: 19
atgacgtatc caaggaggcg ttaccgcaga cgaagacacc gcccccgcag ccatcttggc      60
cagatcctcc gccgccgccc ctggctagtc caccccgcc accgttaccg ctggagaagg     120
aaaaatggca tcttcaacac ccgcctctcc cgcaccatcg ttatactgt caagaaaacc     180 acagtcagaa cgccctcctg gaatgtggac atgatgagat taatattaa tgattttctt     240 cccccaggag ggggctcaag cccctcact gtgccctttg aatactacag aataaggaag    300
gttaaggttg aattctggcc ctgctcccca atcacccagg gtgacagggg agtgagctcc    360
actgctgtta ttctagatga taactttgta acaaaggcca atgcctaac ctatgacccc    420 tatgtaaact actcctcccg ccataccata acccagcct ctcctacca ctcccggtac     480 tttaccccga aacctgtcct tgataggaca atcgattact ccaacccaa taacaaaga    540 aatcaactct ggctgagact acaaactact ggaaatgtag accatgtagg cctcggcact   600
gcgttcgaaa acagtatata cgaccaggac tacaatatcc gtaaccat gtatgtacaa    660 ttcagagaat ttaatcttaa agaccccca cttaaccccta gtga                    705

<210> SEQ ID NO 20
<211> LENGTH: 234
<212> TYPE: PRT
```

<213> ORGANISM: Porcine circovirus

<400> SEQUENCE: 20

Met Thr Tyr Pro Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Thr Thr Val Arg Thr
    50                  55                  60

Pro Ser Trp Asn Val Asp Met Met Arg Phe Asn Ile Asn Asp Phe Leu
65                  70                  75                  80

Pro Pro Gly Gly Gly Ser Ser Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Ser Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230

<210> SEQ ID NO 21
<211> LENGTH: 234
<212> TYPE: DNA
<213> ORGANISM: Porcine circovirus

<400> SEQUENCE: 21
tttcttcccc caggaggggg ctcaagcccc ctcactgtgc cctttgaata ctacagaata      60
aggaaggtta aggttgaatt ctggccctgc tccccaatca cccagggtga caggggagtg    120
agctccactg ctgttattct agatgataac tttgtaacaa aggccaatgc cctaacctat    180 gaccccctatg taaactactc ctcccgccat accataaccc agcccttctc ctac         234

<210> SEQ ID NO 22
<211> LENGTH: 78
<212> TYPE: PRT
<213> ORGANISM: Porcine circovirus

<400> SEQUENCE: 22

Phe Leu Pro Pro Gly Gly Gly Ser Ser Pro Leu Thr Val Pro Phe Glu
1               5                   10                  15

Tyr Tyr Arg Ile Arg Lys Val Lys Val Glu Phe Trp Pro Cys Ser Pro
            20                  25                  30

```
Ile Thr Gln Gly Asp Arg Gly Val Ser Ser Thr Ala Val Ile Leu Asp
         35                  40                  45

Asp Asn Phe Val Thr Lys Ala Asn Ala Leu Thr Tyr Asp Pro Tyr Val
 50                  55                  60

Asn Tyr Ser Ser Arg His Thr Ile Thr Gln Pro Phe Ser Tyr
 65                  70                  75
```

```
<210> SEQ ID NO 23
<211> LENGTH: 31
<212> TYPE: DNA
<213> ORGANISM: Artificial Sequence
<220> FEATURE:
<223> OTHER INFORMATION: Forward primer for PCV2 ORF2 F1

<400> SEQUENCE: 23
cccaagcttg catgacgtat ccaaggaggc g                              31

<210> SEQ ID NO 24
<211> LENGTH: 31
<212> TYPE: DNA
<213> ORGANISM: Artificial Sequence
<220> FEATURE:
<223> OTHER INFORMATION: Reverse primer for PCV2 2a ORF2 F1

<400> SEQUENCE: 24
ccgctcgagg ggtttaagtg gggggtcttt a                              31

<210> SEQ ID NO 25
<211> LENGTH: 31
<212> TYPE: DNA
<213> ORGANISM: Artificial Sequence
<220> FEATURE:
<223> OTHER INFORMATION: Forward primer for PCV2 2a ORF2 F2

<400> SEQUENCE: 25
cccaagcttg ctttgttccc ccgggagggg g                              31

<210> SEQ ID NO 26
<211> LENGTH: 31
<212> TYPE: DNA
<213> ORGANISM: Artificial Sequence
<220> FEATURE:
<223> OTHER INFORMATION: Reverse primer for PCV2 2a ORF2 F2

<400> SEQUENCE: 26
ccgctcgagg taggagaagg gttgggggat t                              31

<210> SEQ ID NO 27
<211> LENGTH: 31
<212> TYPE: DNA
<213> ORGANISM: Artificial Sequence
<220> FEATURE:
<223> OTHER INFORMATION: Forward primer for PCV2 2a ORF2 F3

<400> SEQUENCE: 27
cccaagcttg ccactcccgg tactttaccc c                              31

<210> SEQ ID NO 28
<211> LENGTH: 31
<212> TYPE: DNA
<213> ORGANISM: Artificial Sequence
<220> FEATURE:
<223> OTHER INFORMATION: Reverse primer for PCV2 2a ORF2 F3

<400> SEQUENCE: 28
```

```
ccgctcgagg tcgttaatat taaatctcat c                                    31

<210> SEQ ID NO 29
<211> LENGTH: 31
<212> TYPE: DNA
<213> ORGANISM: Artificial Sequence
<220> FEATURE:
<223> OTHER INFORMATION: Forward primer for PCV2 2a ORF2 F4

<400> SEQUENCE: 29
cccaagcttg cggagtgggc tccactgctg t                                    31

<210> SEQ ID NO 30
<211> LENGTH: 48
<212> TYPE: DNA
<213> ORGANISM: Escherichia coli

<400> SEQUENCE: 30
ctcaaaaaag acgaactgag agatgaactg aaagacgaac tgtaatga                  48

<210> SEQ ID NO 31
<211> LENGTH: 14
<212> TYPE: PRT
<213> ORGANISM: Escherichia coli

<400> SEQUENCE: 31

Leu Lys Lys Asp Glu Leu Arg Asp Glu Leu Lys Asp Glu Leu
1               5                   10

<210> SEQ ID NO 32
<211> LENGTH: 44
<212> TYPE: DNA
<213> ORGANISM: Artificial Sequence
<220> FEATURE:
<223> OTHER INFORMATION: Forward primer for KDEL

<400> SEQUENCE: 32
cccaagcttc tcaaaaaaga cgaactgaga gatgaactga aaga                      44

<210> SEQ ID NO 33
<211> LENGTH: 31
<212> TYPE: DNA
<213> ORGANISM: Artificial Sequence
<220> FEATURE:
<223> OTHER INFORMATION: Reverse primer for KDEL

<400> SEQUENCE: 33
gtgctcgagc agttcgtctt tcagttcatc t                                    31

<210> SEQ ID NO 34
<211> LENGTH: 1116
<212> TYPE: DNA
<213> ORGANISM: Pseudomonas aeruginosa
<300> PUBLICATION INFORMATION:
<308> DATABASE ACCESSION NUMBER: Genbank / K01397
<309> DATABASE ENTRY DATE: 2002-02-11
<313> RELEVANT RESIDUES IN SEQ ID NO: (821)..(1936)

<400> SEQUENCE: 34
gccgaagaag ctttcgacct ctggaacgaa tgcgccaaag cctgcgtgct cgacctcaag     60
gacggcgtgc gttccagccg catgagcgtc gacccggcca tcgccgacac caacggccag    120
ggcgtgctgc actactccat ggtcctggag ggcggcaacg acgcgctcaa gctggccatc    180
gacaacgccc tcagcatcac cagcgacggc ctgaccatcc gcctcgaagg cggcgtcgag    240
```

```
ccgaacaagc cggtgcgcta cagctacacg cgccaggcgc gcggcagttg gtcgctgaac    300
tggctggtac cgatcggcca cgagaagccc tcgaacatca aggtgttcat ccacgaactg    360
aacgccggca accagctcag ccacatgtcg ccgatctaca ccaccgagat gggcgacgag    420
ttgctagcga agctggcgcg cgatgccacc ttcttcgtca gggcgcacga gagcaacgag    480
atgcagccga cgctcgccat cagccatgcc ggggtcagcg tggtcatggc ccagacccag    540
ccgcgccggg aaaagcgctg gagcgaatgg gccagcggca aggtgttgtg cctgctcgac    600
ccgctggacg gggtctacaa ctacctcgcc cagcaacgct gcaacctcga cgatacctgg    660
gaaggcaaga tctaccgggt gctcgccggc aacccggcga agcatgacct ggacatcaaa    720
cccacggtca tcagtcatcg cctgcacttt cccgagggcg gcagcctggc cgcgctgacc    780
gcgcaccagg cttgccacct gccgctggag actttcaccc gtcatcgcca gccgcgcggc    840
tgggaacaac tggagcagtg cggctatccg gtgcagcggc tggtcgccct ctacctggcg    900
gcgcggctgt cgtggaacca ggtcgaccag gtgatccgca acgccctggc cagccccggc    960
agcggcggcg acctaggcga agcgatccgc gagcagccgg agcaggcccg tctggccctg   1020
accctggccg ccgccgagag cgagcgcttc atccggcagg gcaccggcaa cgacgaggcc   1080
ggcgcggcca cgccgacgt ggtgagcctg acctgc                              1116
```

<210> SEQ ID NO 35
<211> LENGTH: 372
<212> TYPE: PRT
<213> ORGANISM: Pseudomonas aeruginosa

<400> SEQUENCE: 35

```
Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Thr Glu Met Gly Asp Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220
```

-continued

```
Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
            245                 250                 255

Ala Ala Leu Thr Ala His Gln Ala Cys His Leu Pro Leu Glu Thr Phe
        260                 265                 270

Thr Arg His Arg Gln Pro Arg Gly Trp Glu Gln Leu Glu Gln Cys Gly
    275                 280                 285

Tyr Pro Val Gln Arg Leu Val Ala Leu Tyr Leu Ala Ala Arg Leu Ser
290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Ile Arg
            340                 345                 350

Gln Gly Thr Gly Asn Asp Glu Ala Gly Ala Ala Asn Ala Asp Val Val
        355                 360                 365

Ser Leu Thr Cys
    370

<210> SEQ ID NO 36
<211> LENGTH: 23
<212> TYPE: DNA
<213> ORGANISM: Artificial Sequence
<220> FEATURE:
<223> OTHER INFORMATION: Forward primer for PE

<400> SEQUENCE: 36
cgggatccga agaagcgttc gac                                           23

<210> SEQ ID NO 37
<211> LENGTH: 32
<212> TYPE: DNA
<213> ORGANISM: Artificial Sequence
<220> FEATURE:
<223> OTHER INFORMATION: Reverse primer for PE

<400> SEQUENCE: 37
cggaattcga gctcgcaggt caggctcacc ac                                 32

<210> SEQ ID NO 38
<211> LENGTH: 28
<212> TYPE: DNA
<213> ORGANISM: Artificial Sequence
<220> FEATURE:
<223> OTHER INFORMATION: Forward primer for PCV2 2a ORF2 F1

<400> SEQUENCE: 38
cgagctcttt gttccccgg gagggggg                                       28

<210> SEQ ID NO 39
<211> LENGTH: 31
<212> TYPE: DNA
<213> ORGANISM: Artificial Sequence
<220> FEATURE:
<223> OTHER INFORMATION: Reverse primer for PCV2 2a ORF2 F1

<400> SEQUENCE: 39
cccaagcttg taggagaagg gttgggggat t                                  31
```

<210> SEQ ID NO 40
<211> LENGTH: 1413
<212> TYPE: DNA
<213> ORGANISM: Artificial Sequence
<220> FEATURE:
<223> OTHER INFORMATION: Combined DNA sequence of PE, PCV2 2a ORF2-F2, and KDEL

<400> SEQUENCE: 40

```
ggatccgaag aagcgttcga cctctggaac gaatgcgcca agcctgcgt gctcgacctc    60
aaggacggcg tgcgttccag ccgcatgagc gtcgacccgg ccatcgccga caccaacggc   120
cagggcgtgc tgcactactc catggtcctg gagggcggca cgacgcgct caagctggcc   180
atcgacaacg ccctcagcat caccagcgac ggcctgacca tccgcctcga aggcggcgtc   240
gagccgaaca gccggtgcg ctacagctac acgcgccagg cgcgcggcag ttggtcgctg   300
aactggctgg taccgatcgg ccacgagaag ccctcgaaca tcaaggtgtt catccacgaa   360
ctgaacgccg caaccagct cagccacatg tcgccgatct acaccaccga gatgggcgac   420
gagttgctag cgaagctggc gcgcgatgcc accttcttcg tcagggcgca cgagagcaac   480
gagatgcagc cgacgctcgc catcagccat gccggggtca gcgtggtcat ggcccagacc   540
cagccgcgcc gggaaaagcg ctggagcgaa tgggccagcg gcaaggtgtt gtgcctgctc   600
gacccgctgg acggggtcta caactacctc gcccagcaac gctgcaacct cgacgatacc   660
tgggaaggca agatctaccg ggtgctcgcc ggcaacccgg cgaagcatga cctggacatc   720
aaacccacgg tcatcagtca tcgcctgcac tttcccgagg gcggcagcct ggccgcgctg   780
accgcgcacc aggcttgcca cctgccgctg gagactttca cccgtcatcg ccagccgcgc   840
ggctgggaac aactggagca gtgcggctat ccggtgcagc ggctggtcgc cctctacctg   900
gcggcgcggc tgtcgtggaa ccaggtcgac caggtgatcc gcaacgccct ggccagcccc   960
ggcagcggcg gcgacctagg cgaagcgatc cgcgagcagc cggagcaggc ccgtctggcc  1020
ctgaccctgg ccgccgccga gagcgagcgc ttcatccggc agggcaccgg caacgacgag  1080
gccggcgcgg ccaacgccga cgtggtgagc ctgacctgcg agctctttgt tcccccggga  1140
gggggggacca acaaaatctc tatacccttt gaatactaca gaataagaaa ggttaaggtt  1200
gaattctggc cctgctcccc aatcacccag ggtgacaggg agtgggctc cactgctgtt  1260
attctagatg ataactttgt aactaaggcc acagccctaa cctatgaccc ctatgtaaac  1320
tactcctccc gccatacaat cccccaaccc ttctcctaca gcttctcaa aaaagacgaa  1380
ctgagagatg aactgaaaga cgaactgctc gag                              1413
```

<210> SEQ ID NO 41
<211> LENGTH: 471
<212> TYPE: PRT
<213> ORGANISM: Artificial Sequence
<220> FEATURE:
<223> OTHER INFORMATION: Combined amino acid sequence of PE, PCV2 2a ORF2-F2, and KDEL

<400> SEQUENCE: 41

```
Gly Ser Glu Glu Ala Phe Asp Leu Trp Asn Glu Cys Ala Lys Ala Cys
 1               5                  10                  15

Val Leu Asp Leu Lys Asp Gly Val Ar

```
Val Leu Glu Gly Gly Asn Asp Ala Leu Lys Leu Ala Ile Asp Asn Ala
 50                  55                  60

Leu Ser Ile Thr Ser Asp Gly Leu Thr Ile Arg Leu Glu Gly Gly Val
 65                  70                  75                  80

Glu Pro Asn Lys Pro Val Arg Tyr Ser Tyr Thr Arg Gln Ala Arg Gly
                 85                  90                  95

Ser Trp Ser Leu Asn Trp Leu Val Pro Ile Gly His Glu Lys Pro Ser
            100                 105                 110

Asn Ile Lys Val Phe Ile His Glu Leu Asn Ala Gly Asn Gln Leu Ser
        115                 120                 125

His Met Ser Pro Ile Tyr Thr Thr Glu Met Gly Asp Glu Leu Leu Ala
130                 135                 140

Lys Leu Ala Arg Asp Ala Thr Phe Phe Val Arg Ala His Glu Ser Asn
145                 150                 155                 160

Glu Met Gln Pro Thr Leu Ala Ile Ser His Ala Gly Val Ser Val Val
                165                 170                 175

Met Ala Gln Thr Gln Pro Arg Arg Glu Lys Arg Trp Ser Glu Trp Ala
            180                 185                 190

Ser Gly Lys Val Leu Cys Leu Leu Asp Pro Leu Asp Gly Val Tyr Asn
        195                 200                 205

Tyr Leu Ala Gln Gln Arg Cys Asn Leu Asp Asp Thr Trp Glu Gly Lys
210                 215                 220

Ile Tyr Arg Val Leu Ala Gly Asn Pro Ala Lys His Asp Leu Asp Ile
225                 230                 235                 240

Lys Pro Thr Val Ile Ser His Arg Leu His Phe Pro Glu Gly Gly Ser
                245                 250                 255

Leu Ala Ala Leu Thr Ala His Gln Ala Cys His Leu Pro Leu Glu Thr
            260                 265                 270

Phe Thr Arg His Arg Gln Pro Arg Gly Trp Glu Gln Leu Glu Gln Cys
        275                 280                 285

Gly Tyr Pro Val Gln Arg Leu Val Ala Leu Tyr Leu Ala Ala Arg Leu
290                 295                 300

Ser Trp Asn Gln Val Asp Gln Val Ile Arg Asn Ala Leu Ala Ser Pro
305                 310                 315                 320

Gly Ser Gly Gly Asp Leu Gly Glu Ala Ile Arg Glu Gln Pro Glu Gln
                325                 330                 335

Ala Arg Leu Ala Leu Thr Leu Ala Ala Ala Glu Ser Glu Arg Phe Ile
            340                 345                 350

Arg Gln Gly Thr Gly Asn Asp Glu Ala Gly Ala Ala Asn Ala Asp Val
        355                 360                 365

Val Ser Leu Thr Cys Glu Leu Phe Val Pro Pro Gly Gly Thr Asn
370                 375                 380

Lys Ile Ser Ile Pro Phe Glu Tyr Tyr Arg Ile Arg Lys Val Lys Val
385                 390                 395                 400

Glu Phe Trp Pro Cys Ser Pro Ile Thr Gln Gly Asp Arg Gly Val Gly
                405                 410                 415

Ser Thr Ala Val Ile Leu Asp Asp Asn Phe Val Thr Lys Ala Thr Ala
            420                 425                 430

Leu Thr Tyr Asp Pro Tyr Val Asn Tyr Ser Ser Arg His Thr Ile Pro
        435                 440                 445

Gln Pro Phe Ser Tyr Lys Leu Leu Lys Asp Glu Leu Arg Asp Glu
450                 455                 460

Leu Lys Asp Glu Leu Leu Glu
```

<210> SEQ ID NO 42
<211> LENGTH: 28
<212> TYPE: DNA
<213> ORGANISM: Artificial Sequence
<220> FEATURE:
<223> OTHER INFORMATION: Forward primer for PCV2 2b ORF2-F2

<400> SEQUENCE: 42
cgagctcttt cttcccccag gaggggc                                28

<210> SEQ ID NO 43
<211> LENGTH: 30
<212> TYPE: DNA
<213> ORGANISM: Artificial Sequence
<220> FEATURE:
<223> OTHER INFORMATION: Reverse primer for PCV2 2b ORF2-F2

<400> SEQUENCE: 43
cccaagcttg taggagaagg gctgggttat                             30

<210> SEQ ID NO 44
<211> LENGTH: 1413
<212> TYPE: DNA
<213> ORGANISM: Artificial Sequence
<220> FEATURE:
<223> OTHER INFORMATION: Combined DNA sequence of PE, PCV2 2b ORF2-F2,
and KDEL

<400> SEQUENCE: 44
ggatccgaag aagcgttcga cctctggaac gaatgcgcca aagcctgcgt gctcgacctc 60
aaggacggcg tgcgttccag ccgcatgagc gtcgacccgg ccatcgccga caccaacggc 120
cagggcgtgc tgcactactc catggtcctg gagggcggca acgacgcgct caagctggcc 180
atcgacaacg ccctcagcat caccagcgac ggcctgacca tccgcctcga aggcggcgtc 240
gagccgaaca agccggtgcg ctacagctac acgcgccagg cgcgcggcag ttggtcgctg 300
aactggctgg taccgatcgg ccacgagaag ccctcgaaca tcaaggtgtt catccacgaa 360
ctgaacgccg gcaaccagct cagccacatg tcgccgatct acaccaccga gatgggcgac 420
gagttgctag cgaagctggc gcgcgatgcc accttcttcg tcagggcgca cgagagcaac 480
gagatgcagc cgacgctcgc catcagccat gccggggtca gcgtggtcat ggcccagacc 540
cagccgcgcc gggaaaagcg ctggagcgaa tgggccagcg gcaaggtgtt gtgcctgctc 600
gacccgctgg acggggtcta caactacctc gcccagcaac gctgcaacct cgacgatacc 660
tgggaaggca agatctaccg ggtgctcgcc ggcaacccgg cgaagcatga cctggacatc 720
aaacccacgg tcatcagtca tcgcctgcac tttcccgagg gcggcagcct ggccgcgctg 780
accgcgcacc aggcttgcca cctgccgctg gagactttca cccgtcatcg ccagccgcgc 840
ggctgggaac aactggagca gtgcggctat ccggtgcagc ggctggtcgc cctctacctg 900
gcggcgcggc tgtcgtggaa ccaggtcgac caggtgatcc gcaacgccct ggccagcccc 960
ggcagcggcg gcgacctagg cgaagcgatc cgcgagcagc cggagcaggc ccgtctggcc 1020
ctgaccctgg ccgccgccga gagcgagcgc ttcatccggc agggcaccgg caacgacgag 1080
gccggcgcgg ccaacgccga cgtggtgagc ctgacctgcg agctctttct tcccccagga 1140
gggggctcaa acccccgctc tgtgcccttt gaatactaca gaataagaaa ggttaaggtt 1200
gaattctggc cctgctcccc gatcacccag ggtgacaggg gagtgggctc cagtgctgtt 1260

-continued

```
attctagatg ataactttgt aacaaaggcc acagccctca cctatgaccc ctatgtaaac    1320
tactcctccc gccataccat aacccagccc ttctcctaca agcttctcaa aaaagacgaa    1380
ctgagagatg aactgaaaga cgaactgctc gag                                 1413
```

<210> SEQ ID NO 45
<211> LENGTH: 471
<212> TYPE: PRT
<213> ORGANISM: Artificial Sequence
<220> FEATURE:
<223> OTHER INFORMATION: Combined amino acid sequence of PE, PCV2 2b
      ORF2-F2, and KDEL

<400> SEQUENCE: 45

```
Gly Ser Glu Glu Ala Phe Asp Leu Trp Asn Glu Cys Ala Lys Ala Cys
1               5                   10                  15

Val Leu Asp Leu Lys Asp Gly Val Arg Ser Ser Arg Met Ser Val Asp
            20                  25                  30

Pro Ala Ile Ala Asp Thr Asn Gly Gln Gly Val Leu His Tyr Ser Met
        35                  40                  45

Val Leu Glu Gly Gly Asn Asp Ala Leu Lys Leu Ala Ile Asp Asn Ala
    50                  55                  60

Leu Ser Ile Thr Ser Asp Gly Leu Thr Ile Arg Leu Glu Gly Gly Val
65                  70                  75                  80

Glu Pro Asn Lys Pro Val Arg Tyr Ser Tyr Thr Arg Gln Ala Arg Gly
                85                  90                  95

Ser Trp Ser Leu Asn Trp Leu Val Pro Ile Gly His Glu Lys Pro Ser
            100                 105                 110

Asn Ile Lys Val Phe Ile His Glu Leu Asn Ala Gly Asn Gln Leu Ser
        115                 120                 125

His Met Ser Pro Ile Tyr Thr Thr Glu Met Gly Asp Glu Leu Leu Ala
    130                 135                 140

Lys Leu Ala Arg Asp Ala Thr Phe Phe Val Arg Ala His Glu Ser Asn
145                 150                 155                 160

Glu Met Gln Pro Thr Leu Ala Ile Ser His Ala Gly Val Ser Val Val
                165                 170                 175

Met Ala Gln Thr Gln Pro Arg Arg Glu Lys Arg Trp Ser Glu Trp Ala
            180                 185                 190

Ser Gly Lys Val Leu Cys Leu Leu Asp Pro Leu Asp Gly Val Tyr Asn
        195                 200                 205

Tyr Leu Ala Gln Gln Arg Cys Asn Leu Asp Asp Thr Trp Glu Gly Lys
    210                 215                 220

Ile Tyr Arg Val Leu Ala Gly Asn Pro Ala Lys His Asp Leu Asp Ile
225                 230                 235                 240

Lys Pro Thr Val Ile Ser His Arg Leu His Phe Pro Glu Gly Gly Ser
                245                 250                 255

Leu Ala Ala Leu Thr Ala His Gln Ala Cys His Leu Pro Leu Glu Thr
            260                 265                 270

Phe Thr Arg His Arg Gln Pro Arg Gly Trp Glu Gln Leu Glu Gln Cys
        275                 280                 285

Gly Tyr Pro Val Gln Arg Leu Val Ala Leu Tyr Leu Ala Ala Arg Leu
    290                 295                 300

Ser Trp Asn Gln Val Asp Gln Val Ile Arg Asn Ala Leu Ala Ser Pro
305                 310                 315                 320

Gly Ser Gly Gly Asp Leu Gly Glu Ala Ile Arg Glu Gln Pro Glu Gln
                325                 330                 335
```

-continued

```
Ala Arg Leu Ala Leu Thr Leu Ala Ala Ala Glu Ser Glu Arg Phe Ile
            340                 345                 350

Arg Gln Gly Thr Gly Asn Asp Glu Ala Gly Ala Ala Asn Ala Asp Val
        355                 360                 365

Val Ser Leu Thr Cys Glu Leu Phe Leu Pro Pro Gly Gly Gly Ser Asn
    370                 375                 380

Pro Arg Ser Val Pro Phe Glu Tyr Tyr Arg Ile Arg Lys Val Lys Val
385                 390                 395                 400

Glu Phe Trp Pro Cys Ser Pro Ile Thr Gln Gly Asp Arg Gly Val Gly
                405                 410                 415

Ser Ser Ala Val Ile Leu Asp Asp Asn Phe Val Thr Lys Ala Thr Ala
            420                 425                 430

Leu Thr Tyr Asp Pro Tyr Val Asn Tyr Ser Ser Arg His Thr Ile Thr
        435                 440                 445

Gln Pro Phe Ser Tyr Lys Leu Leu Lys Lys Asp Glu Leu Arg Asp Glu
    450                 455                 460

Leu Lys Asp Glu Leu Leu Glu
465                 470

<210> SEQ ID NO 46
<211> LENGTH: 28
<212> TYPE: DNA
<213> ORGANISM: Artificial Sequence
<220> FEATURE:
<223> OTHER INFORMATION: Forward primer for PCV2 2d ORF2-F2

<400> SEQUENCE: 46
cgagctcttt cttcccccag gagggggc                                        28

<210> SEQ ID NO 47
<211> LENGTH: 30
<212> TYPE: DNA
<213> ORGANISM: Artificial Sequence
<220> FEATURE:
<223> OTHER INFORMATION: Reverse primer for PCV2 2d ORF2-F2

<400> SEQUENCE: 47
cccaagcttg taggagaagg gctgggttat                                      30

<210> SEQ ID NO 48
<211> LENGTH: 1413
<212> TYPE: DNA
<213> ORGANISM: Artificial Sequence
<220> FEATURE:
<223> OTHER INFORMATION: Combined DNA sequence of PE, PCV2 2d ORF2-F2,
      and KDEL

<400> SEQUENCE: 48
ggatccgaag aagcgttcga cctctggaac gaatgcgcca aagcctgcgt gctcgacctc      60
aaggacggcg tgcgttccag ccgcatgagc gtcgacccgg ccatcgccga caccaacggc     120
cagggcgtgc tgcactactc catggtcctg gagggcggca acgacgcgct caagctggcc     180
atcgacaacg ccctcagcat caccagcgac ggcctgacca tccgcctcga aggcggcgtc     240
gagccgaaca agccggtgcg ctacagctac acgcgccagg cgcgcggcag ttggtcgctg     300
aactggctgg taccgatcgg ccacgagaag ccctcgaaca tcaaggtgtt catccacgaa     360
ctgaacgccg gcaaccagct cagccacatg tcgccgatct acaccaccga gatgggcgac     420
gagttgctag cgaagctggc gcgcgatgcc accttcttcg tcagggcgca cgagagcaac     480
```

```
gagatgcagc cgacgctcgc catcagccat gccggggtca gcgtggtcat ggcccagacc    540
cagccgcgcc gggaaaagcg ctggagcgaa tgggccagcg caaggtgtt gtgcctgctc     600 gacccgctgg acggggtcta caactacctc gcccagcaac gctgcaacct cgacgatacc    660
tgggaaggca agatctaccg ggtgctcgcc ggcaacccgg cgaagcatga cctggacatc    720
aaacccacgg tcatcagtca tcgcctgcac tttcccgagg gcggcagcct ggccgcgctg    780
accgcgcacc aggcttgcca cctgccgctg gagactttca cccgtcatcg ccagccgcgc    840
ggctgggaac aactggagca gtgcggctat ccggtgcagc ggctggtcgc cctctacctg    900
gcggcgcggc tgtcgtggaa ccaggtcgac caggtgatcc gcaacgccct ggccagcccc    960
ggcagcggcg gcgacctagg cgaagcgatc cgcgagcagc cggagcaggc ccgtctggcc   1020
ctgaccctgg ccgccgccga gagcgagcgc ttcatccggc agggcaccgg caacgacgag   1080
gccggcgcgg ccaacgccga cgtggtgagc ctgacctgcg agctctttct tccccagga   1140 gggggctcaa gcccctcac tgtgcccttt gaatactaca gaataaggaa ggttaaggtt    1200
gaattctggc cctgctcccc aatcacccag ggtgacaggg gagtgagctc cactgctgtt   1260
attctagatg ataactttgt aacaaaggcc aatgccctaa cctatgaccc ctatgtaaac   1320
tactcctccc gccataccat aacccagccc ttctcctaca gcttctcaa aaaagacgaa    1380 ctgagagatg aactgaaaga cgaactgctc gag                                 1413
```

<210> SEQ ID NO 49
<211> LENGTH: 471
<212> TYPE: PRT
<213> ORGANISM: Artificial Sequence
<220> FEATURE:
<223> OTHER INFORMATION: Combined amino acid sequence of PE, PCV2 2d
      ORF2-F2, and KDEL

<400> SEQUENCE: 49

```
Gly Ser Glu Glu Ala Phe Asp Leu Trp Asn Glu Cys Ala Lys Ala Cys
1               5                   10                  15

Val Le

```
Ser Gly Lys Val Leu Cys Leu Leu Asp Pro Leu Asp Gly Val Tyr Asn
        195                 200                 205
Tyr Leu Ala Gln Gln Arg Cys Asn Leu Asp Asp Thr Trp Glu Gly Lys
    210                 215                 220
Ile Tyr Arg Val Leu Ala Gly Asn Pro Ala Lys His Asp Leu Asp Ile
225                 230                 235                 240
Lys Pro Thr Val Ile Ser His Arg Leu His Phe Pro Glu Gly Gly Ser
                245                 250                 255
Leu Ala Ala Leu Thr Ala His Gln Ala Cys His Leu Pro Leu Glu Thr
            260                 265                 270
Phe Thr Arg His Arg Gln Pro Arg Gly Trp Glu Gln Leu Glu Gln Cys
        275                 280                 285
Gly Tyr Pro Val Gln Arg Leu Val Ala Leu Tyr Leu Ala Ala Arg Leu
    290                 295                 300
Ser Trp Asn Gln Val Asp Gln Val Ile Arg Asn Ala Leu Ala Ser Pro
305                 310                 315                 320
Gly Ser Gly Gly Asp Leu Gly Glu Ala Ile Arg Glu Gln Pro Glu Gln
                325                 330                 335
Ala Arg Leu Ala Leu Thr Leu Ala Ala Ala Glu Ser Glu Arg Phe Ile
            340                 345                 350
Arg Gln Gly Thr Gly Asn Asp Glu Ala Gly Ala Ala Asn Ala Asp Val
        355                 360                 365
Val Ser Leu Thr Cys Glu Leu Phe Leu Pro Pro Gly Gly Gly Ser Ser
    370                 375                 380
Pro Leu Thr Val Pro Phe Glu Tyr Tyr Arg Ile Arg Lys Val Lys Val
385                 390                 395                 400
Glu Phe Trp Pro Cys Ser Pro Ile Thr Gln Gly Asp Arg Gly Val Ser
                405                 410                 415
Ser Thr Ala Val Ile Leu Asp Asp Asn Phe Val Thr Lys Ala Asn Ala
            420                 425                 430
Leu Thr Tyr Asp Pro Tyr Val Asn Tyr Ser Ser Arg His Thr Ile Thr
        435                 440                 445
Gln Pro Phe Ser Tyr Lys Leu Leu Lys Lys Asp Glu Leu Arg Asp Glu
    450                 455                 460
Leu Lys Asp Glu Leu Leu Glu
465                 470

<210> SEQ ID NO 50
<211> LENGTH: 705
<212> TYPE: DNA
<213> ORGANISM: Porcine circovirus

<400> SEQUENCE: 50
atgacgtatc caaggaggcg ttaccggaga agaagacacc gccccgcag ccatcttggc      60 catatcctcc gccgccgccc ctggctcgtc caccccgcc accgctaccg ttggagaagg     120
aaaaatggaa tcttcaatgc ccgcctctcc cgctcctttg tttataccgt taatgcctca     180
caggtctcac caccctcttg ggcggtggac atgatgagat ttaatattaa ccaatttctt     240
cccccaggag ggggctcaaa cccctcact gtgcccttttg aatactacag aataagaaag     300
gttaaagtgg aattctttgc aagatccccc atcacccaag gtgacagggg agtgggctcc     360
actgctgtta ttctaaatga taactttgta acaaaggcca cagccctaac ctatgacccc     420
tatgtaaact actcctcccg ccataccata acccaaccct ctcctacca ctcccgctac     480 tttacccca aacctgtcct tgattccact attgattact ccaaccaaa taacaaaga      540
```

-continued

| | | | | |
|---|---|---|---|---|
| aatcagctgt | ggatgagact | acaaactact | ggaaatgtag | accatgtagg | cctcggacac | 600 |
| gcctttcaaa | acagtacaaa | tgcccaggcc | tacaatgtcc | gtgtaaccat | gtatgtacaa | 660 |
| ttcagagaat | taatcttaa | agacccccca | cttaaccta | agtga | | 705 |

<210> SEQ ID NO 51
<211> LENGTH: 234
<212> TYPE: PRT
<213> ORGANISM: Porcine circovirus

<400> SEQUENCE: 51

Met Thr Tyr Pro Arg Arg Tyr Arg Arg Arg His Arg Pro Arg
1               5                   10                  15

Ser His Leu Gly His Ile Leu Arg Arg Pro Trp Leu Val His Pro
            20                  25                  30

Arg His Arg Tyr Arg Trp Arg Arg Lys Asn Gly Ile Phe Asn Ala Arg
        35                  40                  45

Leu Ser Arg Ser Phe Val Tyr Thr Val Asn Ala Ser Gln Val Ser Pro
    50                  55                  60

Pro Ser Trp Ala Val Asp Met Met Arg Phe Asn Ile Asn Gln Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Phe Ala Arg Ser Pro Ile Thr
            100                 105                 110

Gln Gly Asp Arg Gly Val Gly Ser Thr Ala Val Ile Leu Asn Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Met Arg Leu Gln Thr Thr Gly Asn
            180                 185                 190

Val Asp His Val Gly Leu Gly His Ala Phe Gln Asn Ser Thr Asn Ala
        195                 200                 205

Gln Ala Tyr Asn Val Arg Val Thr Met Tyr Val Gln Phe Arg Glu Phe
    210                 215                 220

Asn Leu Lys Asp Pro Pro Leu Asn Pro Lys
225                 230

<210> SEQ ID NO 52
<211> LENGTH: 702
<212> TYPE: DNA
<213> ORGANISM: Porcine circovirus

<400> SEQUENCE: 52

| | | | | |
|---|---|---|---|---|
| atgacgtatc | caaggaggcg | ttaccggaga | agaagacacc | gcccccgcag | ccatcttggc | 60 |
| catatcctcc | gccgccgccc | ctggctcgtc | caccccgcc | accgttaccg | ctggagaagg | 120 |
| aaaaatggca | ttttcaacag | ccgcctctcc | cgcaccttcg | gatatactgt | caaggctacc | 180 |
| acagtcacaa | cgccctcctg | ggcggtggac | atgctgagat | tcaatattga | cgactttctt | 240 |
| cccccgggag | ggggaccaa | caaaatctct | atacccttg | agtactacag | aataagaaag | 300 |
| gttaaggttg | aattctggcc | ctgctcccca | atcacccagg | gtgacagggg | agttggatcc | 360 |

```
agtgctgtaa ttctagatga taactttttc cctaagtcca cagccctaac ctatgacccc      420
tacgtaaact actcctcccg ccataccata ccccagccct ctcctacca ctcccgctac       480 tttaccccca aacctgtcct tgattccacc attgattact ccaaccaaa taacaaaagg       540 aatcagctgt ggatgagaat tcaaaccagt aaaaatgtag accacgtagg cctcggcact      600
gcgttcgaaa acagtaaata cgaccaggac tacaatatcc gtgtaaccat gtatgtacaa      660
ttcagagaat taatcttaa agaccccca cttaaaccct aa                          702
```

<210> SEQ ID NO 53
<211> LENGTH: 233
<212> TYPE: PRT
<213> ORGANISM: Porcine circovirus

<400> SEQUENCE: 53

```
Met Thr Tyr Pro Arg Arg Tyr Arg Arg Arg His Arg Pro Arg
1               5                   10                  15
Ser His Leu Gly His Ile Leu Arg Arg Arg Pro Trp Leu Val His Pro
            20                  25                  30
Arg His Arg Tyr Arg Trp Arg Arg Lys Asn Gly Ile Phe Asn Ser Arg
        35                  40                  45
Leu Ser Arg Thr Phe Gly Tyr Thr Val Lys Ala Thr Thr Val Thr Thr
    50                  55                  60
Pro Ser Trp Ala Val Asp Met Leu Arg Phe Asn Ile Asp Asp Phe Leu
65                  70                  75                  80
Pro Pro Gly Gly Gly Thr Asn Lys Ile Ser Ile Pro Phe Glu Tyr Tyr
                85                  90                  95
Arg Ile Arg Lys Val Lys Val Glu Phe Trp Pro Cys Ser Pro Ile Thr
            100                 105                 110
Gln Gly Asp Arg Gly Val Gly Ser Ser Ala Val Ile Leu Asp Asp Asn
        115                 120                 125
Phe Phe Pro Lys Ser Thr Ala Leu Thr Tyr Asp Pro Tyr Val Asn Tyr
    130                 135                 140
Ser Ser Arg His Thr Ile Pro Gln Pro Phe Ser Tyr His Ser Arg Tyr
145                 150                 155                 160
Phe Thr Pro Lys Pro Val Leu Asp Ser Thr Ile Asp Tyr Phe Gln Pro
                165                 170                 175
Asn Asn Lys Arg Asn Gln Leu Trp Met Arg Ile Gln Thr Ser Lys Asn
            180                 185                 190
Val Asp His Val Gly Leu Gly Thr Ala Phe Glu Asn Ser Lys Tyr Asp
        195                 200                 205
Gln Asp Tyr Asn Ile Arg Val Thr Met Tyr Val Gln Phe Arg Glu Phe
    210                 215                 220
Asn Leu Lys Asp Pro Pro Leu Lys Pro
225                 230
```

<210> SEQ ID NO 54
<211> LENGTH: 471
<212> TYPE: DNA
<213> ORGANISM: Porcine circovirus

<400> SEQUENCE: 54

```
tttcttcccc caggaggggg ctcaaacccc ctcactgtgc cctttgaata ctacagaata      60 agaaggtta agtggaatt ctttgcaaga tcccccatca cccaaggtga caggggagtg       120
ggctccactg ctgttattct aaatgataac tttgtaacaa aggccacagc cctaacctat     180
```

```
gaccccctatg taaactactc ctcccgccat accataaccc aaccttctc ctaccactcc    240 cgctacttta cccccaaacc tgtccttgat tccactattg attacttcca accaaataac    300
aaaagaaatc agctgtggat gagactacaa actactggaa atgtagacca tgtaggcctc    360
ggacacgcct ttcaaaacag tacaaatgcc caggcctaca atgtccgtgt aaccatgtat    420
gtacaattca gagaatttaa tcttaaagac cccccactta accctaagtg a             471
```

<210> SEQ ID NO 55
<211> LENGTH: 156
<212> TYPE: PRT
<213> ORGANISM: Porcine circovirus

<400> SEQUENCE: 55

```
Phe Leu Pro Pro Gly Gly Gly Ser Asn Pro Leu Thr Val Pro Phe Glu
1               5                   10                  15

Tyr Tyr Arg Ile Arg Lys Val Lys Val Glu Phe Phe Ala Arg Ser Pro
            20                  25                  30

Ile Thr Gln Gly Asp Arg Gly Val Gly Ser Thr Ala Val Ile Leu Asn
        35                  40                  45

Asp Asn Phe Val Thr Lys Ala Thr Ala Leu Thr Tyr Asp Pro Tyr Val
    50                  55                  60

Asn Tyr Ser Ser Arg His Thr Ile Thr Gln Pro Phe Ser Tyr His Ser
65                  70                  75                  80

Arg Tyr Phe Thr Pro Lys Pro Val Leu Asp Ser Thr Ile Asp Tyr Phe
                85                  90                  95

Gln Pro Asn Asn Lys Arg Asn Gln Leu Trp Met Arg Leu Gln Thr Thr
            100                 105                 110

Gly Asn Val Asp His Val Gly Leu Gly His Ala Phe Gln Asn Ser Thr
        115                 120                 125

Asn Ala Gln Ala Tyr Asn Val Arg Val Thr Met Tyr Val Gln Phe Arg
    130                 135                 140

Glu Phe Asn Leu Lys Asp Pro Pro Leu Asn Pro Lys
145                 150                 155
```

<210> SEQ ID NO 56
<211> LENGTH: 468
<212> TYPE: DNA
<213> ORGANISM: Porcine circovirus

<400> SEQUENCE: 56

```
tttcttcccc cgggaggggg gaccaacaaa atctctatac cctttgagta ctacagaata     60
agaaaggtta aggttgaatt ctggccctgc tccccaatca cccagggtga caggggagtt    120
ggatccagtg ctgtaattct agatgataac tttttcccta gtccacagc cctaacctat    180 gaccccctacg taaactactc ctcccgccat accataccc agcccttctc ctaccactcc    240
cgctacttta cccccaaacc tgtccttgat tccaccattg attacttcca accaaataac    300
aaaaggaatc agctgtggat gagaattcaa accagtaaaa atgtagacca cgtaggcctc    360
ggcactgcgt tcgaaaacag taaatacgac caggactaca atatccgtgt aaccatgtat    420
gtacaattca gagaatttaa tcttaaagac cccccactta aaccctaa                 468
```

<210> SEQ ID NO 57
<211> LENGTH: 155
<212> TYPE: PRT
<213> ORGANISM: Porcine circovirus

```
<400> SEQUENCE: 57

Phe Leu Pro Pro Gly Gly Thr Asn Lys Ile Ser Ile Pro Phe Glu
1               5                   10                  15

Tyr Tyr Arg Ile Arg Lys Val Lys Val Glu Phe Trp Pro Cys Ser Pro
                20                  25                  30

Ile Thr Gln Gly Asp Arg Gly Val Gly Ser Ser Ala Val Ile Leu Asp
            35                  40                  45

Asp Asn Phe Phe Pro Lys Ser Thr Ala Leu Thr Tyr Asp Pro Tyr Val
    50                  55                  60

Asn Tyr Ser Ser Arg His Thr Ile Pro Gln Pro Phe Ser Tyr His Ser
65                  70                  75                  80

Arg Tyr Phe Thr Pro Lys Pro Val Leu Asp Ser Thr Ile Asp Tyr Phe
                85                  90                  95

Gln Pro Asn Asn Lys Arg Asn Gln Leu Trp Met Arg Ile Gln Thr Ser
                100                 105                 110

Lys Asn Val Asp His Val Gly Leu Gly Thr Ala Phe Glu Asn Ser Lys
            115                 120                 125

Tyr Asp Gln Asp Tyr Asn Ile Arg Val Thr Met Tyr Val Gln Phe Arg
    130                 135                 140

Glu Phe Asn Leu Lys Asp Pro Pro Leu Lys Pro
145                 150                 155
```